(12) United States Patent
Pate et al.

(10) Patent No.: US 9,921,170 B2
(45) Date of Patent: Mar. 20, 2018

(54) APPARATUS AND TECHNIQUES FOR FOURIER TRANSFORM MILLIMETER-WAVE SPECTROSCOPY

(71) Applicant: University of Virginia Patent Foundation, Charlottesville, VA (US)

(72) Inventors: Brooks Hart Pate, Charlottesville, VA (US); Amanda Steber, Charlottesville, VA (US); Brent Harris, Charlottesville, VA (US); Kevin K. Lehmann, Crozet, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 14/898,077

(22) PCT Filed: Jun. 12, 2014

(86) PCT No.: PCT/US2014/042094
§ 371 (c)(1),
(2) Date: Dec. 11, 2015

(87) PCT Pub. No.: WO2014/201230
PCT Pub. Date: Dec. 18, 2014

(65) Prior Publication Data
US 2016/0131600 A1 May 12, 2016

Related U.S. Application Data

(60) Provisional application No. 61/835,179, filed on Jun. 14, 2013.

(51) Int. Cl.
*G01J 5/02* (2006.01)
*G01N 22/00* (2006.01)
(Continued)

(52) U.S. Cl.
CPC .............. *G01N 22/00* (2013.01); *G01J 3/453* (2013.01); *G01N 21/3586* (2013.01)

(58) Field of Classification Search
CPC .... G01J 3/453; G01J 3/02; G01N 2021/3595; G01N 21/3563; G01N 21/35
See application file for complete search history.

(56) References Cited

U.S. PATENT DOCUMENTS

| | | | | |
|---|---|---|---|---|
| 3,909,705 A | * | 9/1975 | Tschopp | G01R 33/4616 324/307 |
| 4,464,570 A | | 8/1984 | Allemann et al. | |

(Continued)

FOREIGN PATENT DOCUMENTS

| | | |
|---|---|---|
| CN | 101512286 A | 8/2009 |
| CN | 103583003 A | 2/2014 |

(Continued)

OTHER PUBLICATIONS

Smith et al. ("A 140 GHz pulsed EPR/212 MHz NMR spectrometer for DNP studies" www.elsevier.com, Journal of Magnetic Resonance 223 (2012) p. 170-179).*

(Continued)

*Primary Examiner* — David Porta
*Assistant Examiner* — Mamadou Faye
(74) *Attorney, Agent, or Firm* — Schwegman Lundberg & Woessner P.A.

(57) ABSTRACT

Examples herein include apparatus and techniques that can be used to perform rotational spectroscopy on gas-phase samples. Such techniques can include using a spectrometer providing frequency synthesis and pulse modulation to provide excitation (e.g., pump or probe pulses) of a gas-phase sample at mm-wave frequencies. Synthesis of such mm-wave frequencies can include use of a frequency multiplier, such as an active multiplier chain (AMC). A free (Continued)

induction decay (FID) elicited by the excitation or other time-domain information can be obtained from the sample, such as down-converted and digitized. A frequency domain representation of the digitized information, such as a Fourier transformed representation, can be used to provide a rotational spectrum.

20 Claims, 12 Drawing Sheets

(51) Int. Cl.
    *G01J 3/453*     (2006.01)
    *G01N 21/3586*   (2014.01)

(56)         References Cited

U.S. PATENT DOCUMENTS

| | | | |
|---|---|---|---|
| 4,967,160 | A | 10/1990 | Quievy et al. |
| 5,047,636 | A | 9/1991 | Farrar et al. |
| 5,508,661 | A | 4/1996 | Keane et al. |
| 8,300,228 | B2 | 10/2012 | Marks et al. |
| 8,748,822 | B1 | 6/2014 | Gerecht et al. |
| 8,873,043 | B2 | 10/2014 | Pate et al. |
| 9,046,462 | B2 | 6/2015 | Pate et al. |
| 9,442,079 | B2 | 9/2016 | Pate et al. |
| 9,482,577 | B2 | 11/2016 | Pate et al. |
| 2004/0007666 | A1* | 1/2004 | Griffey ............... H01J 49/0077 250/282 |
| 2005/0058218 | A1 | 3/2005 | Jenkins |
| 2005/0168735 | A1 | 8/2005 | Boppart et al. |
| 2006/0049981 | A1 | 3/2006 | Merkel et al. |
| 2007/0223936 | A1 | 9/2007 | Babbitt et al. |
| 2008/0224908 | A1 | 9/2008 | Li et al. |
| 2008/0285606 | A1 | 11/2008 | Kippenberg et al. |
| 2009/0073432 | A1 | 3/2009 | Jalali et al. |
| 2009/0161092 | A1 | 6/2009 | Zanni et al. |
| 2010/0046003 | A1 | 2/2010 | Le Floch et al. |
| 2010/0290025 | A1 | 11/2010 | Parker |
| 2013/0154611 | A1 | 6/2013 | Pate et al. |
| 2013/0265573 | A1 | 10/2013 | Pate et al. |
| 2015/0253261 | A1 | 9/2015 | Pate et al. |
| 2015/0260575 | A1 | 9/2015 | Pate et al. |
| 2017/0089831 | A1 | 3/2017 | Pate et al. |

FOREIGN PATENT DOCUMENTS

| | | |
|---|---|---|
| JP | 2016521859 A | 7/2016 |
| TW | 201510504 A | 3/2015 |
| WO | WO-2011160013 A1 | 12/2011 |
| WO | WO-2012129089 A1 | 9/2012 |
| WO | WO-2014201230 A1 | 12/2014 |

OTHER PUBLICATIONS

"U.S. Appl. No. 15/255,-36, Preliminary Amendment filed Dec. 15, 2016", 7 pgs.
"U.S. Appl. No. 15/255,036, Non Final Office Action dated Jan. 12, 2017", 9 pgs.
"U.S. Appl. No. 15/338,851, Notice of Allowance dated May 2, 2017", 10 pgs.
"U.S. Appl. No. 15/338,851, Preliminary Amendment filed Mar. 10, 2017", 72 pgs.
"European Application Serial No. 14811595.9, Supplemental European Search Report dated Feb. 3, 2017", 6 pgs.
Yi-Da, Hsieh, et al., "Terahertz Comb Spectroscopy Traceable to Microwave Frequency Standard", IEEE Transactions on Terahertz Science and Technology, IEEE, Piscataway, NJ, USA, XP011506303, ISSN: 2156-342X, (Apr. 29, 2013), 322-330.
"International Application Serial No. PCT/US2014/042094, International Search Report dated Nov. 20, 2014", 4 pgs.
"International Application Serial No. PCT/US2014/042094, Invitation to Pay Additional Fees and Partial Search Report dated Sep. 9, 2014", 2 pgs.
"International Application Serial No. PCT/US2014/042094, Written Opinion dated Nov. 20, 2014", 5 pgs.
Campbell, E. J, et al., "The theory of pulsed Fourier transform microwave spectroscopy carried out in a Fabry—Perot cavity: Static gas", J. Chem. Phys., 74, (1981), 813-828.
Crowe, T. W, et al., "Opening the terahertz window with integrated diode circuits", IEEE Journal of Solid-State Circuits, 40(10), (Oct. 2005), 2104-2110.
Drouin, B. J, et al., "Application of cascaded frequency multiplication to molecular spectroscopy", Rev. Sci. Instrum., 76, (2005), 093113.
Ekkers, J., et al., "Pulsed microwave Fourier transform spectrometer", Rev. Sci. Instrum., 47, (1976), 448-454.
Green, Sheldon, "On the amount of information in rotational relaxation experiments with application to microwave transient T1 and T2 rates", J. Chem. Phys., 69, (1978), 4076-4082.
Hahn, E. L., "Spin Echos", Physical Review, 80(1), (1950), 580-594.
Harris, Brent, et al., "Segmented Chirped Pulse Fourier Transform (CP-FT) Millimeter Spectroscopy: Identification of Volatiles by Pure Rotation", Eastern Analytical Symposium & Exposition 2012, (2012), 1 pg.
Hoke, W. E, et al., "The measurement and interpretation of T1 and T2 in the inversion doublets of 15NH3 and the rotational transitions in OCS", J. Chem. Phys., 64, (1976), 5276-5282.
Mata, Santiago, "A broadband Fourier-transform microwave spectrometer with laser ablation source: The rotational spectrum of nicotinic acid", Journal of Molecular Spectroscopy 280: 91-96, (2012), 91-96.
Matton, S., et al., "Terahertz spectroscopy applied to the measurement of strengths and self-broadening coefficients for high-J lines of OCS", Journal of Molecular Spectroscopy, 239(2), (Oct. 2006), 182-189.
Medvedev, Ivan R, et al., "Submillimeter spectroscopy for chemical analysis with absolute specificity", Optics Letters, 35(10), (2010), 1533-1535.
Neese, C. F, et al., "Compact Submillimeter/Terahertz Gas Sensor With Efficient Gas Collection, Preconcentration, and ppt Sensitivity", IEEE Sensors Journal, 12(8), (Aug. 2012), 2565-2574.
Park, Barratt G, et al., "Design and evaluation of a pulsed-jet chirped-pulse milimeter-wave spectrometer for the 70-102 GHz region", AIP The Journal of Chemical Physics 135, 024202, (2011), 1-3.
Pate, B. H, "Chemistry. Taking the pulse of molecular rotational spectroscopy", Science, 333(6045), (Aug. 19, 2011), 947-8.
Petkie, D. T, et al., "A fast scan submillimeter spectroscopic technique", Rev. Sci. Instrum., 68, (1997), 1675-1683.
Smith, Albert A, et al., "A 140 GHz pulsed EPR/212 MHz NMR spectrometer for DNP studies", Journal of Magnetic Resonance 223, [Online]. Retrieved from the Internet: <http://www.sciencedirect.com/science/article/pii/S1090780712002509>, (Jul. 20, 2012), 170-179.
U.S. Appl. No. 14/718,624, filed May 21, 2015, Chirped Pulse Frequency-Domain Comb for Spectroscopy, U.S. Pat. No. 9,442,079.
U.S. Appl. No. 14/494,315, filed Sep. 23, 2014, Segmented Chirped-Pulse Fourier Transform Spectroscopy.
"U.S. Appl. No. 13/704,483, Notice of Allowance dated Feb. 3, 2015", 10 pgs.
"U.S. Appl. No. 13/704,483, Notice of Allowance dated Oct. 9, 2014", 11 pgs.
"U.S. Appl. No. 13/704,483, Preliminary Amendment dated Dec. 14, 2012", 8 pgs.
"U.S. Appl. No. 13/912,548, Notice of Allowance dated Mar. 18, 2014", 12 pgs.
"U.S. Appl. No. 13/912,548, Notice of Allowance dated Jul. 1, 2014", 9 pgs.
"U.S. Appl. No. 14/494,315, Final Office Action dated Dec. 31, 2015", 9 pgs.

(56) References Cited

OTHER PUBLICATIONS

"U.S. Appl. No. 14/494,315, Non Final Office Action dated Jul. 8, 2015", 6 pgs.
"U.S. Appl. No. 14/494,315, Notice of Allowance dated Jul. 29, 2016", 9 pgs.
"U.S. Appl. No. 14/494,315, Response filed May 3, 2016 to Final Office Action dated Dec. 31, 2015", 8 pgs.
"U.S. Appl. No. 14/494,315, Response filed Dec. 7, 2015 to Non Final Office Action dated Jul. 8, 2015", 9 pgs.
"U.S. Appl. No. 14/718,624, Final Office Action dated Dec. 30, 2015", 8 pgs.
"U.S. Appl. No. 14/718,624, Non Final Office Action dated Jul. 16, 2015", 6 pgs.
"U.S. Appl. No. 14/718,624, Notice of Allowance dated Apr. 4, 2016", 12 pgs.
"U.S. Appl. No. 14/718,624, Notice of Allowance dated May 10, 2016", 6 pgs.
"U.S. Appl. No. 14/718,624, Response filed Feb. 29, 2016 to Final Office Action dated Dec. 30, 2015", 11 pgs.
"U.S. Appl. No. 14/718,624, Response filed Oct. 16, 2015 to Non Final Office Action dated Jul. 16, 2015", 7 pgs.
"Chinese Application Serial No. 201280023629.7, Office Action dated Feb. 1, 2016", 16 pgs.
"European Application Serial No. 11796503.8, Extended European Search Report dated Sep. 24, 2015", 8 pgs.
"European Application Serial No. 12761002.0, Extended European Search Report dated Aug. 14, 2014", 6 pgs.
"European Application Serial No. 14811595.9, Response to Communication pursuant to Rules 161(2) and 162 EPC dated Aug. 17, 2016", 20 pgs.
"International Application Serial No. PCT/US2011/040876, Written Opinion dated Oct. 5, 2011", 9 pgs.
"International Application Serial No. PCT/US2011/040876, International Preliminary Report on Patentability dated Jan. 3, 2013", 11 pgs.
"International Application Serial No. PCT/US2011/040876, International Search Report dated Oct. 5, 2011", 2 pgs.
"International Application Serial No. PCT/US2012/029430, International Preliminary Report on Patentability dated Oct. 3, 2013", 8 pgs.
"International Application Serial No. PCT/US2012/029430, International Search Report dated Jul. 11, 2012", 4 pgs.
"International Application Serial No. PCT/US2012/029430, Written Opinion dated Jul. 11, 2012", 6 pgs.
"Tektronix AWG710B", Ananonymous, (Nov. 1, 2002).
Balle, T. J, et al., "Fabry—Perot cavity pulsed Fourier transform microwave spectrometer with a pulsed nozzle particle source", Rev. Sci. Instrum., 52, (1981), 33-45.
De Lucia, Frank C., "The submillimeter: A spectroscopist's view", Journal of Molecular Spectroscopy, 261(1), (May 2010), 1-17.
Dian, B C, et al., "Measuring Picosecond Isomerization Kinetics via Broadband Microwave Spectroscopy", Science, vol. 320, No. 5878, (May 16, 2008), 924-928.
Finneran, I. A, et al., "A direct digital synthesis chirped pulse Fourier transform microwave spectrometer", Rev Sci Instrum., 84(8), (Aug. 2013), 083104.
Gerecht, Eyal, et al., "Recent Progress in Chirped-Pulse Fourier Transform THz Spectroscopy", NIST, (Jun. 23, 2010), 20 pgs.
Gerecht, Eyal, "Recent Progress in Chirped-Pulse Fourier Transform THz spectroscopy (with embedded notes)", NIST, (Apr. 19, 2016), 40 pgs.
Medvedev, I. R, et al., "Chemical analysis in the submillimetre spectral region with a compact solid state system", Analyst, 131(12), (Dec. 2006), 1299-307.
Ozawa, A, et al., "High Harmonic Frequency Combs for High Resolution Spectroscopy", Physical Review Letters, vol. 100, No. 25, (Jun. 1, 2008).
Shipman, Steven, et al., "Waveguide Chirped-Pulse FTMW Spectroscopy", (Jun. 18, 2008), 29 pgs.

Spokas, J. J, et al., "Nuclear Relaxation in Aluminum", Phys. Rev., 113,, (Mar. 15, 1959), 1462.
Steber, Amanda L, et al., "An arbitrary waveform generator based chirped pulse Fourier transform spectrometer operating from 260 to 295 GHz", Journal of Molecular Spectroscopy, 280, Oct. 3-10, 2012.
"International Application Serial No. PCT/US2014/042094, International Preliminary Report on Patentability dated Dec. 23, 2015", 7 pgs.
Brown, G. G, et al., "A broadband Fourier transform microwave spectrometer based on chirped pulse excitation", Rev Sci Instrum., 79(5), (May 2008), 053103.
Brown, Gordon, et al., "The rotational spectrum of epifluorohydrin measured by chirped-pulse Fourier transform microwave spectroscopy", Journal of Molecular Spectroscopy, 238(2), (Aug. 2006), 200-212.
Coddington, Ian, et al., "Time-domain spectroscopy of molecular free-induction decay in the infrared", National Institute of Standards and Technology, (2010), 1395-1397.
Dian, Brian C., et al., "Seeing Is Believing: An 11 GHz molecular beam rotational spectrum (7.5-18.5 GHz) with 100 kHz resolution in 15 us measurement time", International Symposium on Molecular Spectroscopy, (Jun. 20, 2005), 29 pgs.
Douglass, K. O, et al., "Progress towards chirpedpulse Fourier transform THz spectroscopy", 64th International Symposium on Molecular Spectroscopy, Columbus, OH, [Online]. Retrieved from the Internet: <URL: http://hdl.handle.net/1811/46369>, (Jun. 21-25, 2010.), 21 pgs.
Gerecht, E., et al., "Chirped-pulse terahertz spectroscopy for broadband trace gas sensing", Opt Express., 19(9), (Apr. 25, 2011), 8973-84.
Gerecht, Eyal, et al., "Chirped-Pulse Terahertz Spectroscopy for Broadband Tracegas Sensing", National Institute of Standards and Technology, Optical Technology Division, (Jun. 21, 2011), 24 pgs.
Kuyanov-Prozument, K., et al., "Direct Observation of Rydberg—Rydberg Transitions in Calcium Atoms", International Symposium on Molecular Spectroscopy, (Jun. 22, 2010), 20 pgs.
Lesarri, Alberto, et al., "Interplay of Phenol and Isopropyl Isomerism in Propofol from Broadband Chirped-Pulse Microwave Spectroscopy", American Chemical Society, (Sep. 7, 2010), 13417-13424.
Neill, Justin L., et al., "Next generation techniques in the high resolution spectroscopy of biologically relevant molecules", Phys. Chem. Chem. Phys.,13, (2011), 7253-7262.
Neill, Justin L., et al., "Rotational spectroscopy of iodobenzene and iodobenzene—neon with a direct digital 2-8 GHz chirped-pulse Fourier transform microwave spectrometer", Journal Of Molecular Spectroscopy, (2011), 21-29.
Neill, Justin L, et al., "Segmented chirped-pulse Fourier transform submillimeter spectroscopy for broadband gas analysis", Optics Express, 21(17), (2013), 19743-19749.
Neill, Justin L., et al., "Techniques for High-Bandwidth (> 30 GHz) Chirped-Pulse Millimeter/Submillimeter Spectroscopy", (Jun. 23, 2011), 22 pgs.
Park, G. B, et al., "Design and chemical application of chirped-pulse millimeterwave spectroscopy", 64th International Symposium on Molecular Spectroscopy, Columbus, OH,, [Online]. Retrieved from the Internet: <URL: http://hdl.handle.net/1811/38114 >, (41 pgs), Jun. 22-26, 2009.
Prozument, Kirill, "Chirped-Pulse Millimeter-Wave Spectroscopy of Rydberg—Rydberg Transitions", American Physical Society, (2011), 5 pgs.
Shipman, Steven T., et al., "Design and performance of a direct digital chirped-pulse Fourier transform microwave (CP-FTMW) spectrometer operating from 2-8 GHz", International Symposium on Molecular Spectroscopy, (Jun. 18, 2008), 29 pgs.
Twagirayezu, Sylvestre, "Vibrational Coupling Pathways in Methanol As Revealed by Coherence-Converted Population Transfer Fourier Transform Microwave Infrared Double-Resonance Spectroscopy", J. Phys. Chem. A, (2010), 6818-6828.
Zaleski, Daniel P., et al., "A Ka-Band Chirped-Pulse Fourier Transform Microwave Spectrometer", International Symposium on Molecular Spectroscopy, (Jun. 22, 2010), 17 pgs.

(56) References Cited

OTHER PUBLICATIONS

Zaleski, Daniel, et al., "A Ka-band chirped-pulse Fourier transform microwave spectrometer", Article in Journal of Molecular Spectroscopy, (Oct. 2012), 10 pgs.
U.S. Appl. No. 15/255,036, filed Sep. 1, 2016, Chirped Pulse Frequency-Domain Comb for Spectroscopy.
U.S. Appl. No. 15/338,851, filed Oct. 31, 2016, Segmented Chirped-Pulse Fourier Transform Spectroscopy.
"European Application Serial No. 14811595.9, Extended European Search Report dated May 15, 2017", 9 pgs.

* cited by examiner

APPARATUS AND TECHNIQUES FOR FOURIER TRANSFORM MILLIMETER-WAVE SPECTROSCOPY

CLAIM OF PRIORITY

This application claims benefit of priority of U.S. Provisional Patent Application Ser. No. 61/835,179, titled "FOURIER TRANSFORM MILLIMETER-WAVE SPECTROMETER FOR THE ANALYSIS OF GAS MIXTURES," filed on Jun. 14, 2013, which is hereby incorporated by reference herein in its respective entirety.

STATEMENT REGARDING FEDERALLY-SPONSORED RESEARCH OR DEVELOPMENT

This invention was made with government support under Grant No. CHE-1242377 awarded by the National Science Foundation (NSF). The government has certain rights in the invention.

BACKGROUND

Molecular rotational spectroscopy is a technique that offers high chemical selectivity and sensitivity and can be used to analyze mixtures of gas samples. The technique is applicable to volatile species (e.g., having a minimum vapor pressure of about 0.1 Pascal (Pa)). Molecular rotational spectroscopy generally relies on a polar conformation of a molecule for detection (i.e., the molecule has a non-zero dipole moment). For room-temperature samples, a peak of the spectral intensity of a rotational spectrum typically occurs in the range of millimeter-wave ("mm-wave") frequencies (e.g., from about 200 Gigahertz (GHz) to about 1000 GHz), particularly for molecules with 2-10 "heavy" nuclei (non-hydrogen atoms). A molecular rotational spectrum of most molecules will contain multiple, spectrally narrow transitions in any fixed mm-wave frequency range of modest bandwidth (e.g., a bandwidth of about 30 to about 50 GHz). Accordingly, a chemical analysis of a multiple component gas mixture can be made using a single mm-wave frequency range because all species will have spectroscopic transitions in the measurement range. However, the presence of overlapping spectra presents challenges to identifying the rotational spectrum of a single gas mixture component.

OVERVIEW

Trace gas analysis by molecular rotational spectroscopy has a wide range of applications. Such trace gas analysis can be used such as for environmental monitoring of volatile organic compounds (VOCs) or toxic industrial chemicals (TICs), for example, in workplace safety or national security applications. Such trace gas monitoring can also be used to monitor the trace compounds of exhaled breath, offering rapid, non-invasive medical diagnostics tests. In these applications, molecular rotational spectroscopy can provide one or more of sensitivity or chemical selectivity comparable to (or exceeding the performance of) complex analysis methods like gas chromatography—mass spectrometry (GC-MS) with the simplicity of molecular spectroscopy analytical chemistry methods like Fourier transform infrared spectroscopy (FTIR).

In various applications, goals of spectroscopic analysis can include detection of a presence of a series of known compounds in one or more of a minimum amount of time or with a low rate of false positive identifications. Molecular rotational spectrometers operating at mm-wave frequencies can use direct absorption spectroscopy to measure a set of known molecular rotational transitions and quantify the composition of gas mixtures. In this approach, due to the high spectral resolution intrinsic to molecular rotational spectroscopy, the mixture can be directly analyzed without prior chemical separation using techniques like gas chromatography.

An ability to work directly with gas mixtures without separation offers several advantages including reduced recurring costs for operating the spectrometer, lower possibility of cross contamination between measurements, much more rapid response time, and the ability to optimize the analysis process by selecting the order and sensitivity level (through signal averaging time) for each molecule being detected rather than, for example, relying on elution times of the chromatographic separation. Molecular rotational spectroscopy, unlike mass spectrometry, is also generally a non-destructive analysis method making it possible to retrieve the sample after analysis. This feature can be useful in applications where it is desired to archive the samples or, in instances where molecular rotational spectroscopy is used as a rapid, low-cost screening method, to identify samples that require more elaborate testing protocols. Such archival can aid in preserving sample integrity for medical or forensic applications.

The present inventors have, among other things, realized that a time-domain spectroscopy technique can be employed for gas mixture analysis by molecular rotational spectroscopy at mm-wave frequencies. For example, using a pulsed mm-wave excitation source, a sensitivity of the spectrometer can be significantly improved, such as in part using high output powers provided by one or more solid-state active multiplier chains (AMCs) to provide energy in the mm-wave range (e.g., providing mm-wave "light sources"). Spectroscopic transitions can be detected by measuring a coherent emission, which can be referred to as the free induction decay (FID), following a short (e.g., gated) excitation pulse, in a manner similar to techniques used in relation to room-temperature measurements of the rotational spectrum at microwave frequencies.

A frequency domain representation of the transition can be obtained, such as performing a fast Fourier transformation of a digitized time series representative of the coherent emission. Such a coherent Fourier transform technique can be advantageous because an entirety of the emission line shape can be determined using a single observation. Moreover, in a coherent emission approach, emitted light can be detected against essentially zero background because the excitation source is generally disabled during the collection (e.g., mixing, amplification, filtering, and digitizing) of the free induction decay. By contrast, in an absorption spectroscopy approach, several frequency steps corresponding to several measurement acquisitions are generally necessary.

The present inventors have also recognized that the time-domain excitation and emission observation techniques are intrinsically time-resolved, and thus provide new measurement capabilities that significantly enhance the capabilities of molecular rotational spectroscopy as a trace gas analysis tool. The new spectrum analysis capabilities can, for example, include the following:

1) Two-Color Saturation Double-Resonance Spectroscopy

In this example, excitation using two frequencies can be used to establish that two spectroscopic transitions share a common quantized energy level of the same molecule. It can provide information in a manner similar to 2-D magnetic resonance spectroscopy, but using a different apparatus and range of frequencies. The two-color saturation double-resonant technique can significantly reduce a false positive identification rate in gas mixture analysis. Also, this technique can be used for library-free identification of molecules in gas mixtures.

2) Single Color Pulse Echoes

In this example, collisional relaxation rates can be independently determined for transitions in a gas sample. With this information, a measured time-domain FID can be fit to an analytically determined (e.g., simulated) FID, such as an FID calculated using information about a collisional relaxation rate and mass-dependent Doppler dephasing. The fit can then be used to provide a mass estimate for the molecule.

3) One- and Two-Color Population Recovery Measurements

This technique can be implemented in a manner similar to the pulse echo measurement technique mentioned above and can be used to independently measure collisional relaxation rates. In comparison to other techniques, the population recovery technique offers an advantage that it can have higher sensitivity and can be used on weak transitions in the mixture spectrum.

4) One- and Two-Color Variable Pulse Duration Population Transfer Measurements

These examples can include use of a variable duration excitation pulse and can include measurement of a signal of either the driven transition (e.g., "one-color" measurement) or a double-resonance transition (e.g., "two-color" measurement) as a function of pulse duration. A variation of the measured signal can be used to estimate a transition dipole moment of the transition and enables estimation of an absolute concentration of a molecular species—even if the exact molecular identity is unknown.

In support of the techniques above, the present inventors have also developed apparatus. Such apparatus can include solid-state AMC mm-wave sources, such as can be driven by pulse-modulated microwave or radio frequency sources that use integrated circuit (IC)-based frequency synthesizers, such as one or more synthesizers that are generally available for communications applications. A receiver can include one or more analog-to-digital (ADC) ICs for signal digitization, such as following frequency down-conversion using a mm-wave mixer. The apparatus offers a compact, low-cost approach to rotational spectroscopy trace gas detectors in addition to programmable flexibility for a wide range of specific analysis applications.

DETAILED DESCRIPTION

Figure 1:
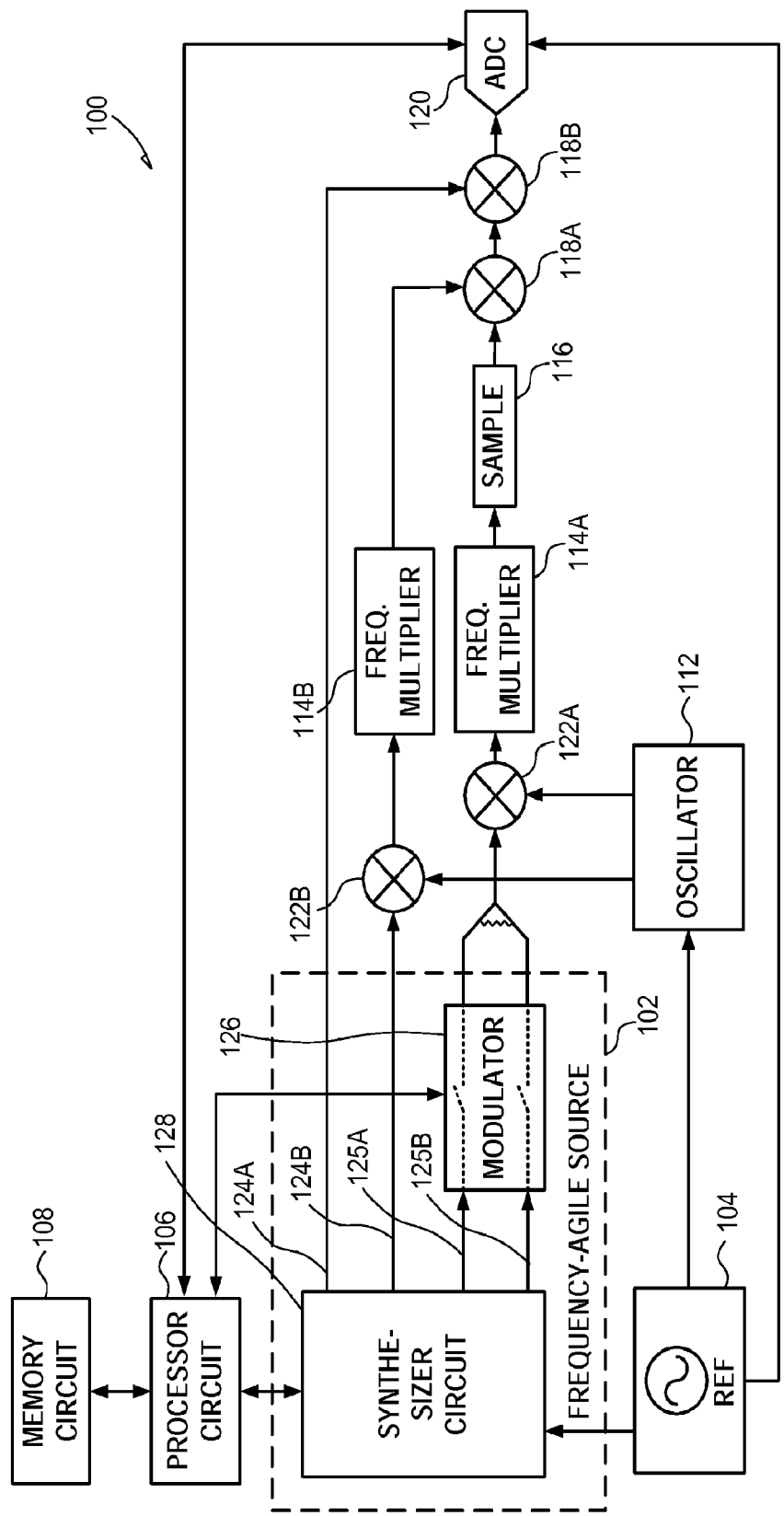
FIG. 1 illustrates generally an example of a system for generating pulse-modulated excitation signals, and for obtaining emission from a sample in response to such excitation, such as for providing a Fourier transform mm-wave spectrometer.

Generally-available techniques for molecular rotational spectroscopy of gas samples at millimeter-wave ("mm-wave") to terahertz ("THz") frequencies generally rely on direct absorption. In such an approach, a molecular rotational spectrum is generally measured by scanning a frequency of the mm-wave/THz light source through a spectral range that contains a spectroscopic transition while monitoring the power of the light that is transmitted through the sample. As the light frequency approaches a "resonant" rotational transition, the molecular gas sample absorbs power from the light source and a reduction in the transmitted power can be detected.

However, such an absorption-based approach has several drawbacks, including the need to slowly scan the light source through the molecular resonance. A rotational transition will absorb light over a narrow range of frequencies, where the peak absorption occurs exactly on resonance. Tracing the reduction of power through such resonance yields the line shape. At each measurement frequency, the dwell time is generally a few times the value of a transition dephasing time ($T_2$) and several frequency points are generally obtained to accurately determine the spectral line shape. Narrow absorption lines (long $T_2$ times) are advantageous to maximize sensitivity and selectivity of the detection, such as corresponding to slow sweep rates, but operating under such conditions is generally balanced against measurement time in this absorption-based approach.

In addition to a sweep-rate limitation, a swept-frequency absorption-based technique measures the molecular spectrum through a reduction in transmitted power, meaning that this absorption signal is detected against an often noisy spectral intensity of the mm-wave light source because such a source must be enabled during the absorption measurement. Reflections of the radiation while passing from source to detector lead to modulations in the transmitted power and such effects can be temperature and pressure dependent, making them difficult to remove from the measurement.

Also, low pressure conditions generally used to measure the high-resolution molecular rotational spectrum of a gas sample using absorption-based techniques can impose a limit to the amount of mm-wave power that can be used in the experiment before the effects of power broadening limit the sensitivity and selectivity thereby limiting the signal-to-noise ratio and thus the detection sensitivity. An additional complication in absorption-based approaches is that an optimum power for a spectral measurement can depend on the molecular properties so respective molecular species generally require a corresponding power setting.

Accordingly, the present inventors have recognized that a time-domain (e.g., time-resolved) pulsed-excitation approach can be used for rotational spectroscopy using pulsed light sources, and such a time-domain approach can overcome the numerous drawbacks observed above.

A spectrometer for gas analysis according to the techniques described herein can generally provide at least two or more separate excitation frequencies, such as selectively outputting a specified one of the frequencies during a given duration. According to various examples, switching between such frequencies can be performed in times much shorter than an intrinsic measurement time, and a pulse duration of one or more excitation pulses can be varied. Such variable-width pulses can be used for a variety of time-domain measurements for the analysis of gas mixtures by molecular rotational spectroscopy. Following pulsed excitation of the gas sample, a molecular emission, or free induction decay ("FID"), can be measured using a high-speed digitizer, such as following frequency down-conversion using a subharmonic mm-wave mixer.

Figure 2:
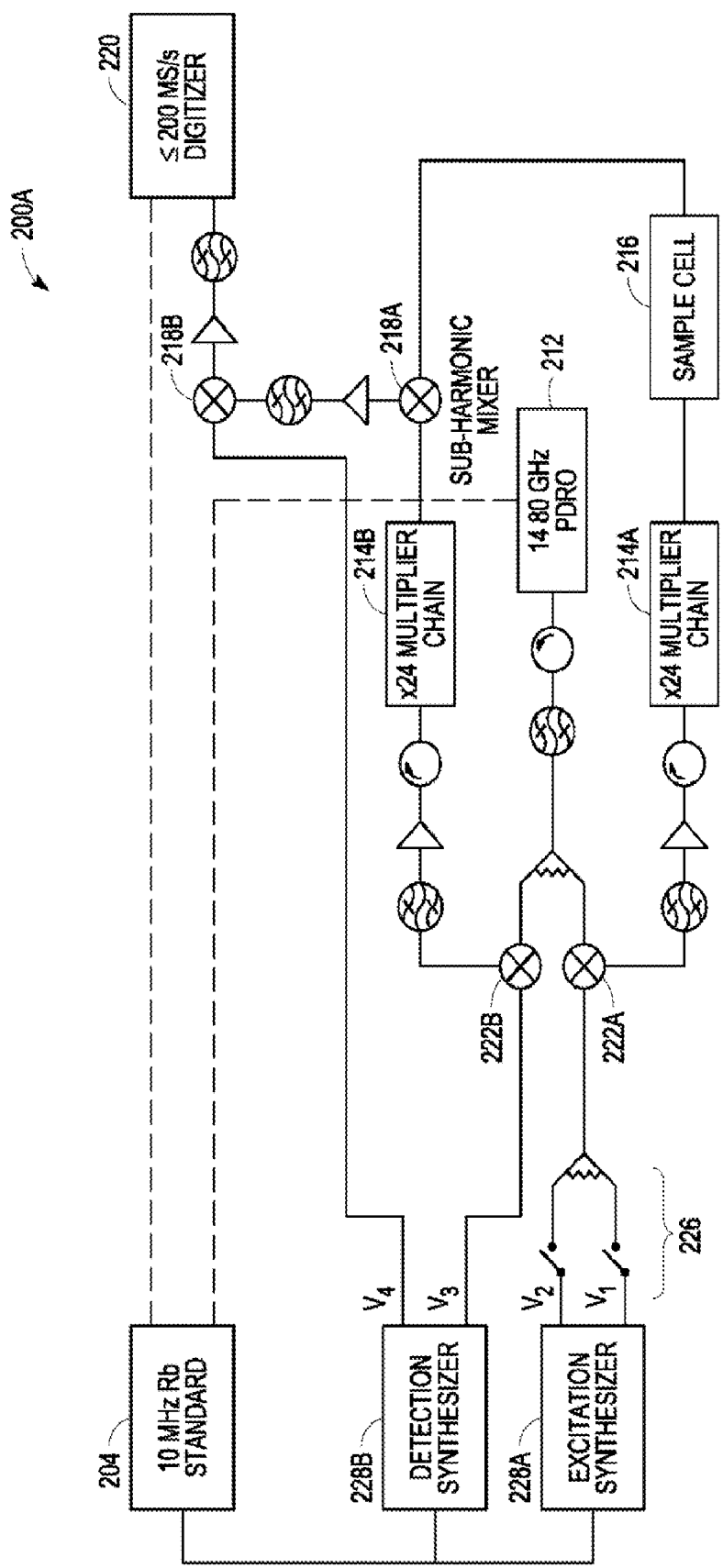
FIG. 2 illustrates generally an illustrative example of a system for generating pulse-modulated excitation signals, and for obtaining emission from a sample in response to such excitation, such as for providing a Fourier transform mm-wave spectrometer.

Measurement sensitivity can be increased by collecting multiple FIDs and averaging them in the time domain, thereby reducing the noise level for a better signal to noise ratio. The frequency-domain spectrum can be obtained from the FID by fast Fourier transformation (FFT) or other transformation of a time series representing the FID. All frequency sources (including the multiple frequencies of the excitation sources and the frequencies used in the FID detection by down conversion), and the digitizer, can be locked to a high accuracy, low phase noise reference clock (e.g., a 10 MHz reference clock). In an example, such as shown in FIG. 2, a rubidium ("Rb") stabilized crystal oscillator, or Rb clock, can be used as the reference clock. FIGS. 1 and 2 generally illustrate examples of apparatus that can be used to provide a Fourier transform mm-wave spectrometer system.

FIG. 1 illustrates generally an example of a system 100 for generating pulse-modulated excitation signals, and for obtaining emission from a sample in response to such excitation, such as for providing a Fourier transform mm-wave spectrometer. In an example, the system 100 can include at least one processor circuit 106, such as coupled to a memory circuit 108 (or one or more other storage circuits or devices).

The processor circuit 106 can be coupled to a synthesizer circuit 128, such as can include multiple outputs providing one or more fixed or user-adjustable continuous-wave (CW) outputs having specified phase noise and frequency stability. For example, the synthesizer circuit can provide multiple excitation outputs, such as can include a first excitation output 125A and a second excitation output 125B. In an example where the outputs 125A and 125B are CW outputs, a modulator 126 can be included. The modulator can be used to gate the outputs 125A or 125B, such as to provide at least a controllable pulse width and pulse separation (e.g., an independently controllable on-duration and off-duration for each of the CW outputs of the synthesizer 128). In an illustrative example, a first frequency can be provided by the first output 125A, and a second frequency can be provided by the second output 125B. During various portions of a measurement cycle, a pulsed representation of one of the first or second outputs 125A or 125B can be provided to a combiner located at an output of the modulator 126. In this manner, the modulator 126 and synthesizer 128 can provide a low-cost frequency-agile pulse-modulated frequency source. According to various examples, a variety of frequency-agile source circuits can be used, such as can include digital-to-analog (DAC) sources including arbitrary waveform generation capability, direct digital synthesis (DDS) sources configured to provide sinusoidal excitation with a pulsed envelope, or pulse-modulated continuous wave (CW) sources that can include phase-locked synthesizers such as illustrated in the examples of FIGS. 1 and 2.

The output of the combiner can then be upconverted by a first up-conversion mixer 122A, such as coupled to an oscillator 112 to provide a "local oscillator" frequency for the first mixer 122A. The output of the first up-conversion mixer 122A can then be multiplied from a microwave frequency range to a mm-wave frequency range, such as using a first frequency multiplier 114A, such as to excite a gas-phase sample in a sample cell 116.

An emission elicited from a sample within the sample cell 116, such as a molecular free induction decay (FID), can be down-converted using a first down-conversion mixer 118A. In the dual conversion example of FIG. 1, a second down-conversion mixer 118B can be included, such as to further down-convert a first intermediate frequency (IF) representation of the FID to a range of frequencies within the bandwidth of a digitizer (e.g., an analog-to-digital converter 120). Such a range of frequencies need not be baseband, and can include a near-zero (e.g., near-baseband) second IF frequency.

An LO frequency for the second down-conversion mixer 118B can be provided using a first detection output 124A of the synthesizer 128. An LO frequency for the first down-conversion mixer 118A can be provided using a second detection output 124B of the synthesizer 128. In an example where a desired LO frequency is beyond a range of frequencies available from the synthesizer 128, a second up-conversion mixer 122B can be used, such as using an LO frequency provided by the oscillator 112. The output of the second up-conversion mixer 122B can be frequency multiplied by a second frequency multiplier 114B.

As mentioned above, a down-converted emission signal can be provided to input of an ADC 120, within the available bandwidth of the ADC 120. The processor circuit 106 can be configured to estimate a spectrum of the emission signal using information obtained via the ADC 120. The processor circuit can perform instructions stored using the memory circuit 108, such as to implement one or more of the measurement techniques described elsewhere herein.

FIG. 2 illustrates generally an illustrative example of a system 200 for generating pulse-modulated excitation signals, and for obtaining emission from a sample in response to such excitation, such as for providing a Fourier transform mm-wave spectrometer.

As in the example of FIG. 1, FIG. 2 illustrates generally an excitation synthesizer 228A showing, illustratively, a "2-color" output (e.g., providing a respective time-gated or continuous output frequency at a respective channel, such as including two channels). The excitation synthesizer 228 can output both a "pump" excitation pulse and "probe" pulse, such as using the respective outputs $v_1$ and $v_2$. In the example of a CW synthesizer, a modulator 226 can be provided to selectively gate one or more of the synthesizer 228A outputs, along with a combiner to provide the gated outputs to a first up-conversion mixer 222A.

A detection synthesizer 228B can provide output frequencies, such as for use in down-conversion of other signals. For example, the detection synthesizer 228B can operate in continuous mode, such as to provide one signal for each of the heterodyne down-conversion steps using a first down-conversion mixer 218A (e.g., a sub-harmonic mixer) and a second down-conversion mixer 218B. As mentioned above, a "final" intermediate frequency (IF) provided to a digitizer 220 can have both a small frequency and bandwidth so that a relatively low-cost digitizer can be used. For example, a 200 megasample per second (MS/s) digitizer 220 can be used, or a digitizer having a sampling rate less than about 200 MS/s, such as to minimize system complexity or to facilitate cointegration of the digitizer in a commonly-shared module or circuit along with other portions of the system shown in the examples of FIG. 1 or 2.

Respective active multiplier chains can include a ×24 Multiplier Chain 214A to provide an up-converted "pump" or "probe" pulse at a mm-wave range of frequencies, and a ×12 Multiplier Chain 214B to provide a first (IF) LO for the first mixer 218A. An input the ×12 Multiplier Chain 214B can be provided by mixing an output of the detection synthesizer 228B with an LO frequency provided by, for example, a phase-locked dielectric resonator oscillator (PDRO) 212. In various examples, inputs to the multiplier chains 224A or 224B can be provided at least in part instead by one or more digital-to-analog converters or other circuits. For example, synthesizers 228A or 228B can include one or more arbitrary waveform generators or continuous-wave oscillators, such as locked to a frequency standard (e.g., a Rubidium standard 204). As in the example of FIG. 1, other portions of the system 200 can be locked to or otherwise derive a frequency or timing reference from the frequency standard 204. In this manner, phase-coherent excitation can be provided, such as within a measurement cycle, or from cycle-to-cycle in cases where multiple acquisitions are to be performed, such as for purposes of averaging. Aspects of the apparatus of FIGS. 1 and 2 can include the following or can use techniques described in the following examples:

A) Pulse Generation Suitable for Coherent Time Domain Signal Averaging

A molecular emission (FID) for a polarized transition in a room-temperature sample decays by both Doppler dephasing and collisional effects. A decay rate of the latter collisional effects is proportional to the sample pressure while the former Doppler dephasing is pressure-independent. Generally, a decay time for the FID is in the range of about 500-1000 nanoseconds (ns) for the pressures used to obtain a high-resolution rotational spectrum (e.g., about 1 to about 100 millitorr (mTorr) total pressure). In Fourier transform spectroscopy, an excitation pulse is generally specified to include a duration that is on the order of, and usually shorter than, this characteristic decay time. For example, pulse durations of 100-500 ns can typically be used. The examples of FIGS. 1 and 2, and the variations described above can provide such excitation according to one or more specified measurement protocols.

In an example, a single-frequency excitation pulse can be generated by pulse amplitude modulating a CW output of a radio frequency (RF) synthesizer channel, and then providing such modulated output to a mm-wave AMC source. Such modulated pulses have a frequency domain profile including a finite bandwidth determined in part by their pulse duration. Therefore, to provide spectral coverage of a desired band to be interrogated, the systems of FIGS. 1 and 2 can operate at a set of specified fixed frequencies covering specified ranges of bandwidth, where each specified fixed frequency creates a field envelope in the frequency domain as shown illustratively in FIG. 3.

Figure 3:
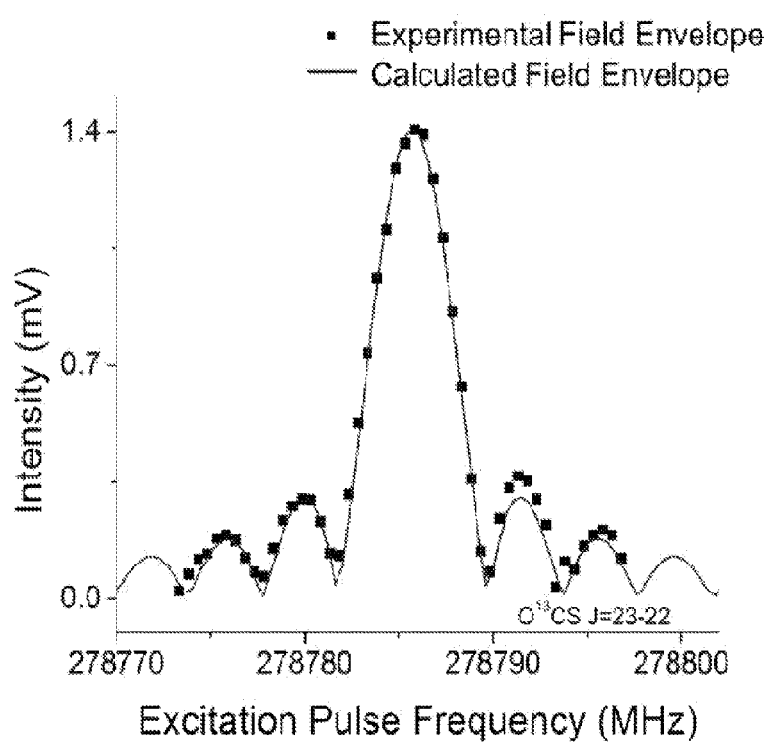
FIG. 3 illustrates generally an illustrative example that can include a field envelope of a short pulse, such as a pulse having energy in the mm-wave frequency range as can be provided by the apparatus of FIG. 1 or 2.

FIG. 3 illustrates generally an illustrative example that can include a field envelope of a short pulse, such as a pulse having energy in the mm-wave frequency range as can be provided by the apparatus of FIG. 1 or 2. The electric field envelope of FIG. 3 shows generally the molecular signal strength as a function of RF input frequency for an excitation pulse of 250 ns duration. As the short excitation pulse is detuned from the resonant frequency for the molecule $O^{13}CS$ J=23-22 (278785.3 MHz), the $O^{13}CS$ transition falls into a weak region of the excitation pulse's electric field envelope. The $O^{13}CS$ signal level (black points in FIG. 3) trace out the effective bandwidth of the excitation pulse, measured and confirmed with calculation to be approximately 5 MHz at full width half maximum.

The sample excitation profile of FIG. 3 illustrates generally a pulse envelope shape corresponding to the Fourier transform of a square wave having a pulse duration of about 250 ns. Effective sample excitation occurs over the central portion of the waveform (which can be represented as the full width half maximum)—providing a frequency span of about 5000 kHz. A shape of the excitation profile can be controlled by changing the temporal shape of the excitation pulse though square pulse excitation, however other time-domain pulse shapes (e.g., windows) can be used such as to modulate or otherwise control the shape of the resulting excitation pulse frequency profile.

In view of the example of FIG. 3, a span of excitation frequencies to measure molecular transitions can be specified such as to include values having a frequency spacing that is less than the central region of the resulting pulse excitation profile in the frequency domain, providing contiguous or overlapping coverage of a desired range of frequencies. Furthermore, a sensitivity of the Fourier transform spectrometer configurations described herein can be attributed at least in part to an ability to average the signals in the time domain. For example, each excitation pulse can start with the same relative phase of the light wave. The excitation pulses can be repeated after each measurement cycle, such as including a measurement cycle defined to include both the excitation pulse and the time to record the FID. In an illustrative example, total measurement cycle times can range between 2-5 microseconds. A series of excitation pulses and corresponding FID time series representations can be acquired at each excitation frequency, and obtained FID time series representations can be averaged in the time domain to provide an averaged time series representation for each excitation frequency.

In this manner, a rotational spectrum of the gas sample over the full spectrometer operating range can then be acquired by performing measurements at a sequential set of excitation frequencies, with or without averaging at each frequency, and concatenating the resulting spectra in the frequency domain.

Precise and repeatable phasing of the excitation pulses and local oscillator frequency used for frequency down conversion can be achieved by using a set of frequencies that all have an integer number of cycles in the measurement time period. For example, if a 4 microsecond measurement cycle is used, then the mm-wave excitation frequencies (and frequency used in the down conversion) occur on multiples of 250 kilohertz (kHz). To achieve this performance, a pulse pattern generator circuit can be included, such as locked to the frequency reference (e.g., a 10 MHz Rb clock). The pulse pattern generator can be used to drive the pulse modulation switch (e.g., modulator 126 as in FIG. 1 or 226 as shown in FIG. 2) on the RF input to the AMC 214A to define pulse durations where selected outputs of the excitation synthesizer are provided to the AMC 214A.

B) Data Collection Using a Pulse Train

Various examples herein include measurements performed as a function of excitation pulse duration or as a function of a delay between pulses (as in the pulse-echo measurement examples). Improved measurement performance can be achieved by using a pulse train that executes these measurements sequentially in a short period of time. Even the basic spectrometer operation of signal averaging a single molecular transition can be implemented using pulse trains.

In an illustrative example, a pulse train can be created using a pulse pattern generator waveform that generates a desired on/off sequence (pulse modulation) to be applied to an output of a synthesizer. The modulators 126 and 226 of FIG. 1 or 2 can be driven by, or can include, for example, a 240 MS/s arbitrary waveform generator (AWG), such as having a 64 million data point memory to create the modulation waveforms. The digitizer used to collect the down-converted representation of the elicited FID can also have a memory depth of 64 million points to capture the time-domain waveform. After measurement, the captured waveform can be transferred to a digital processor circuit that can select each measurement section and perform the spectroscopic analysis, including one or more of averaging or transform (e.g., FFT) operations, for example. This implementation can be highly efficient because one pulse pattern waveform can be applied to modulate any excitation frequency and can, therefore, be created and stored separately.

C) Two-Stage Frequency Downconversion for Lower Background Noise

The spectrometer apparatus of FIGS. 1 and 2 can include a two-stage frequency down conversion process (e.g., a "dual conversion" superheterodyne topology). This approach can reduce the background noise for detection that is related to the behavior of the subharmonic mm-wave mixer (e.g., mixer 218A in FIG. 2) at low frequency (e.g., ~75 MHz). The two-step down-conversion can first translate the mm-wave FID signal to a frequency near 4275 MHz. Following signal filtering, this intermediate signal can be down-converted to about 75 MHz in a second microwave mixing stage (e.g., mixer 218B in FIG. 2). The resulting FID signal can then be digitized, e.g., at 200 Megasamples/s using a 12-bit analog-to-digital converter ("ADC").

Methods for the Analysis of Gas Mixtures Using Fourier Transform Mm-Wave Rotational Spectroscopy A) Detection with High Chemical Selectivity One operational method for the spectrometer apparatus shown in FIG. 1 or 2 can include identification of a known volatile compound through its previously measured rotational spectrum. In this example, the frequencies and strengths of the rotational transitions of the molecule are generally known. For example, several rotational transitions for each chemical species in the frequency operating range of the spectrometer will generally exist. The spectrometer can be programmed to monitor several of these transitions sequentially (e.g., excite the sample at a specified frequency including a known transition and monitor the resulting FID), and the measured intensities at the known transition frequencies can be used to estimate the amount of the species present. A similar approach has been used for spectrometers based on absorption spectroscopy. If the concentrations deduced from different transitions are consistent, this provides strong evidence that the measurement is not significantly affected by spectral overlap, thereby dramatically reducing the possibility of a false positive identification.

Two-Color Double-Resonance Spectroscopy

Figure 4A:
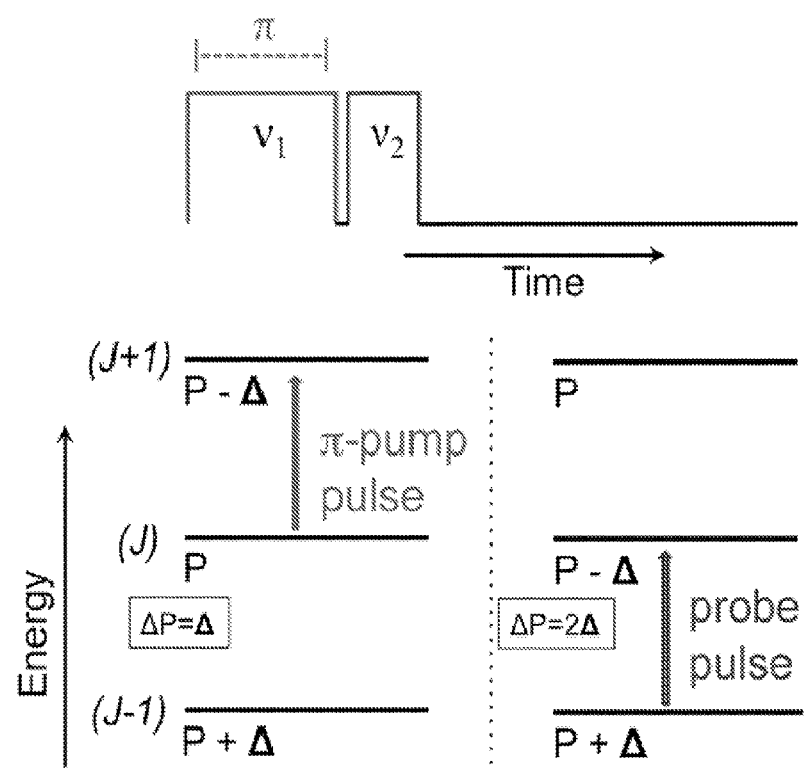
FIG. 4A illustrates generally rotational energy levels and a corresponding coherent double-resonant spectroscopy technique, such as can be performed using the apparatus of FIG. 1 or 2.

FIG. 4A illustrates generally rotational energy levels and a corresponding coherent double-resonant spectroscopy technique, such as can be performed using the apparatus of FIG. 1 or 2, such as can be used as a portion of a measurement technique for double-resonance spectroscopy. A first light pulse (the "pump" pulse) coherently excites a known rotational transition of the molecule of interest. The duration of the pump pulse is adjusted to achieve a "$\pi$-pulse" excitation which has the effect of inverting the populations of the two energy levels involved in the transition. This pulse duration generally provides a maximum double-resonance signal modulation and, in particular, provides larger modulation than can be achieved using incoherent "saturation spectroscopy" that simply equalizes the populations in the two levels. Following the pump pulse (e.g., immediately or almost immediately), a second transition of the molecule is excited (the "probe" pulse) and the FID is then collected. This second transition is chosen so that it shares an energy level in common with the pump transition for a species of interest. Frequency agility of the light source is used because the second pulse (having a different frequency than the first pulse) is applied immediately to the sample before collisions reduce the population inversion achieved by the pump pulse and thereby reduces the signal modulation.

A simple three state energy level diagram is shown illustratively in FIG. 4A, for the quantized rotational kinetic energy states (labelled by the total rotational angular momentum quantum number, J). The selection rules for rotational spectroscopy only allow transitions where J changes by ±1. At thermal equilibrium the three energy levels have different populations (given as $P+\Delta$, P, and $P-\Delta$). For room-temperature mm-wave rotational spectroscopy, the population difference between the energy levels is approximately constant ($\Delta$). The first pulse is resonant with a rotational transition of the molecule of interest. The pulse duration is selected to achieve a $\pi$-pulse excitation which results in population inversion of the levels. The signal in the Fourier transform mm-wave measurement of the "probe" transition is proportional to the population difference. In the absence of the $\pi$-pulse, this population difference is $\Delta$. When the $\pi$-pulse is applied prior to the probe, the population difference doubles to $2\Delta$. The signal modulation caused by double-resonance ($2\Delta-\Delta$) is as large as the original signal. In general, it is not possible to achieve the ideal $\pi$-pulse conditions due to the dependence of the transition moment on the projection of the angular momentum on the molecular axis. However, signal modulations in the 50-80% range are observed using this technique, as shown in other illustrative examples herein.

Figure 4B:
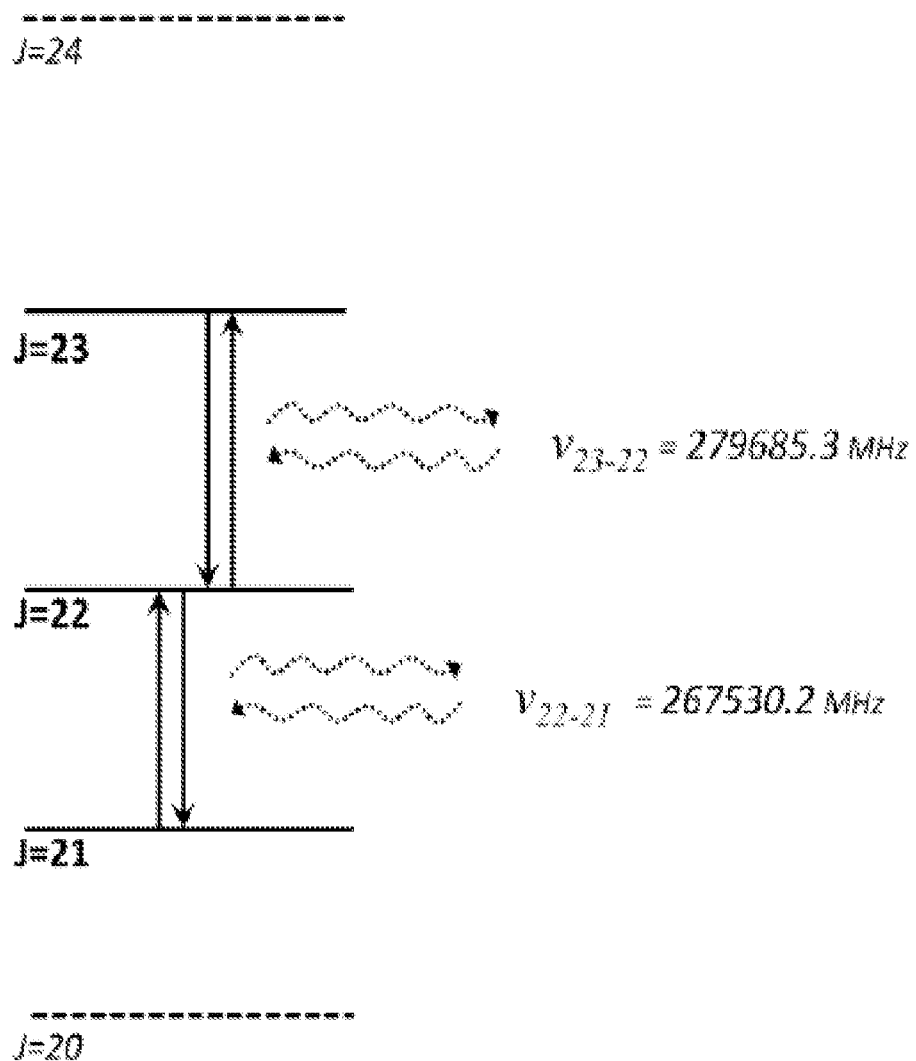
FIG. 4B illustrates generally an illustrative example of discrete mm-wave rotational energy levels, such as depicting a carbonyl sulfide (OCS) manifold.

FIG. 4B illustrates generally an illustrative example of discrete mm-wave rotational energy levels, such as depicting a carbonyl sulfide (OCS) manifold. A higher "J" translates to a higher energy rotation. In double resonance saturation, a "pump" pulse sets up the condition of equal population between two energy levels (e.g., J=23 and J=22). This perturbs the thermally distributed population, and the "probed" transition (e.g., J=22 and J=21) excitation is seen as a signal increase (compared to a single-color excitation) because it shares the "pumped" energy level (e.g., J=22).

However, for complex gas mixtures the rotational spectrum becomes dense and the probability of a random spectral overlap increases, thereby increasing the potential for a false positive detection. Various techniques described herein can reduce the probability of false positive detection by performing two-color, time-domain double-resonance spectroscopy. This measurement is made possible in part by the frequency agility intrinsic to the combination of tunable synthesizers coupled to an AMC, to provide the frequency-agile light source. It allows a near-immediate or immediate switch from pump pulse excitation to probe pulse excitation in the light source.

Figure 5A:
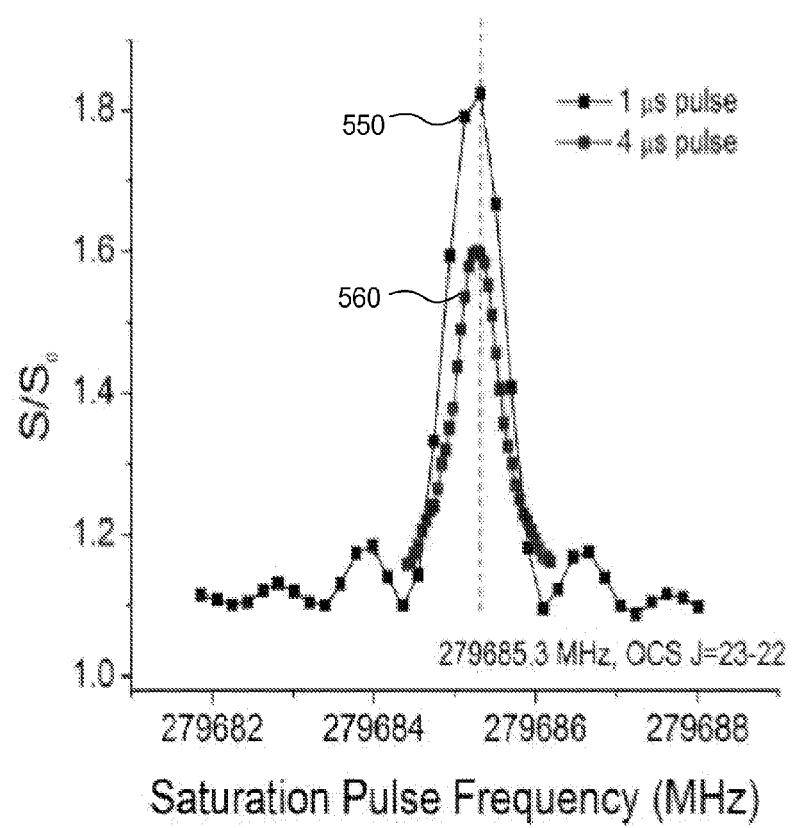
FIG. 5A illustrates generally an illustrative example showing selectivity of a double-resonance modulation spectroscopy technique, including an example of modulation of transition.
Figure 5B:
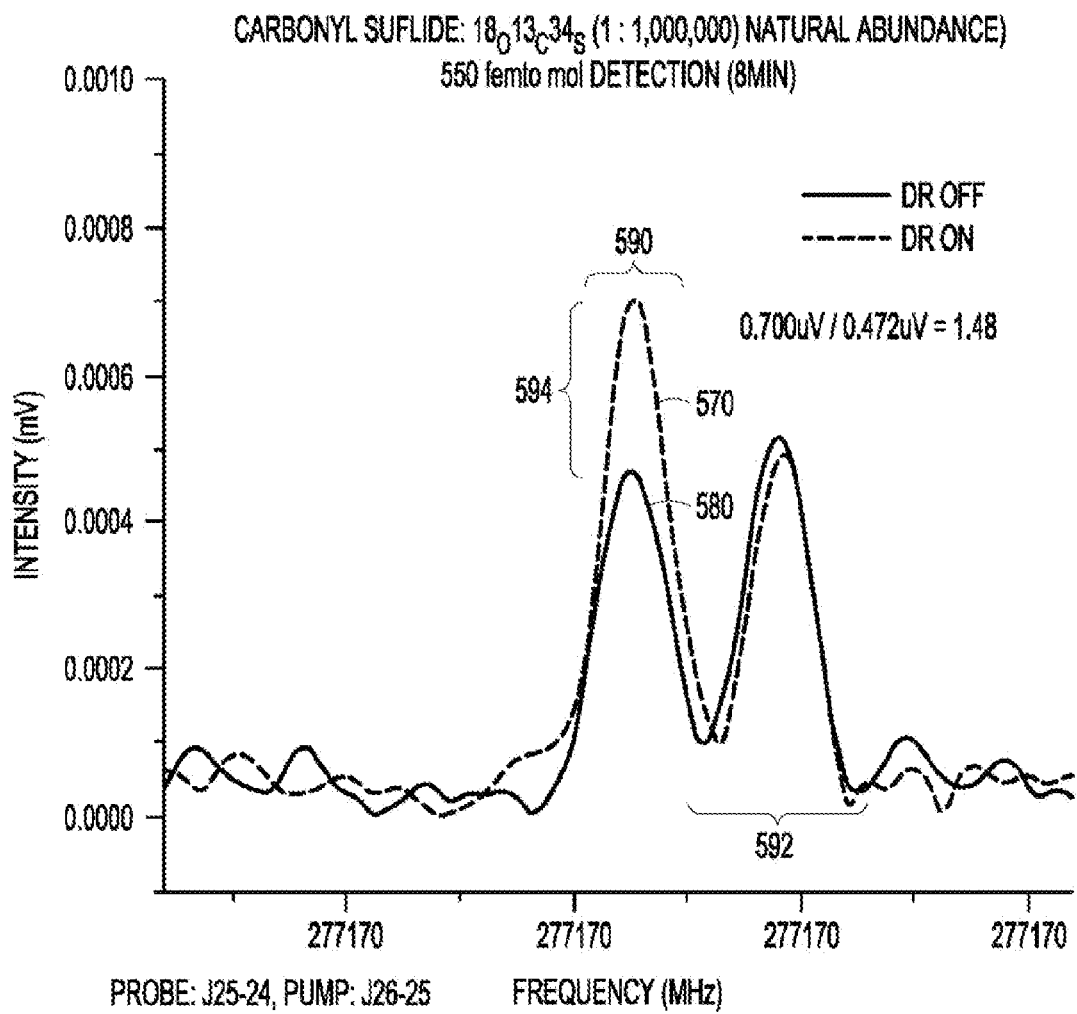
FIG. 5B illustrates generally an illustrative example showing selectivity of a double-resonance modulation spectroscopy technique, including an example of modulation of a specified transition corresponding to a molecule of interest without modulation of an unrelated peak.

FIG. 5A illustrates generally an illustrative example showing selectivity of a double-resonance modulation spectroscopy technique, including an example of modulation of a specified transition. FIG. 5B illustrates generally an illustrative example showing selectivity of a double-resonance modulation spectroscopy technique, including an example of modulation of a specified transition corresponding to a molecule of interest without modulation of an unrelated peak.

In FIG. 5A, with accurate (e.g., near-perfect or perfect) tuning, the pump pulse can induce an 80% increase in the probed transition. Signal modulation of the probed transition (J=22–21) decreases as the pump pulse is detuned from resonance with the "pumped" transition (J=23–22). When a short pump pulse is used, e.g., 1 microsecond (us), the envelope 550 is representative of a power-broadened envelope; with a longer pump pulse (4 us), the envelope 560 is Lorentzian (e.g., comprising a semi-classical power envelope corresponding to a radiating dipole). The width of each feature is no more than about 1 MHz, which is less than a spectral line width. The illustration of FIG. 5A shows that large signal modulation is possible (80%) in this example, using the molecule carbonyl sulfide (OCS), and that the excitation pulse has good frequency selectivity (the double-resonance effect can be observed when the pump frequency is within +1-500 kHz of the exact resonance frequency). This technique illustrates generally the exclusion of the possibility that these two transitions result from random spectral overlaps of the sample.

Moreover, the method permits discrimination using the double-resonance effect where only the transition in double-resonance is modulated even in a presence of a dense spectrum, such as shown illustratively in FIG. 5B. The signal for a probe rotational transition (J=24–J=25) of a minor isotope the molecule carbonyl sulfide ($^{18}O^{13}C^{34}S$, $10^{-6}$ natural abundance, 550 femtomole present in the gas sample) is shown with (as in the plot 570) and without (as in the plot 580) prior application of a π-pulse (resonant with the J=26–J=25 rotational transition). This excitation sequence is illustrated generally in the example of FIG. 4A. Only the transition in the region 590 for the molecule of interest shows signal modulation 594. The higher frequency transition in the region 592, near 277180 MHz is unmodulated.

B) Methods for Separating a Mixture Spectrum and Identifying Unknown Chemical Species Gas analysis by broadband molecular rotational spectroscopy, such as using apparatus and techniques described herein, offers capabilities to identify molecules in the sample that have not been previously characterized by measurement. For example, a sample can be analyzed in cases where there is no "library spectrum" of the unknown molecule for direct identification. Identification of an unknown molecule can include use of experimental techniques to characterize the molecule's geometry (through its rotational constants that are determined by the principal moments-of-inertia), its centrifugal distortion constants (which depend on the force constants for the vibrational normal modes), electronic properties (the dipole moment and its projection on the principal axes), nuclear quadrupole hyperfine structure (for some elements such as chlorine), and mass. One or more of these properties can be estimated to high-accuracy by quantum chemistry so that molecule identification is possible using a computational library (e.g., identifying a molecule using one or more analytically-determined model parameters) instead of relying on previous experimentally-obtained spectra.

Two-Color Saturation Double-Resonance Spectroscopy to Identify a Spectrum

Analysis of an unknown species can be performed by first acquiring a spectrum. The spectrum is includes a set of rotational transitions generated in correspondence to the unknown molecule's rotational kinetic energy levels. Therefore, finding the set of transitions with double-resonance connection can be desirable. Such transitions can be identified using the technique described in FIGS. 4A, 4B, 5A, and 5B. In an example, a single, unassigned transition (e.g., corresponding to an unknown molecular carrier) is selected, and such a transition is checked for double-resonance with other observed transitions with the unknown molecular carrier. The spectrum can ultimately be built up in a bootstrap fashion. Once the spectrum is identified, it can be analyzed using generally-available methods of molecular rotational spectroscopy to determine the rotational constants (A, B, and C) and centrifugal distortion constants. In some examples, this basic structural information can be augmented by the determination of barriers to internal rotation and nuclear quadrupole hyperfine parameters. Once a few "connected" rotational transitions are identified (e.g., three or four), the rotational constants can be estimated for the unknown molecule and used to predict additional transition frequencies that would need to fall in highly restricted frequency intervals thereby speeding up the automated spectrum analysis procedure.

Figures 6A, 6B:
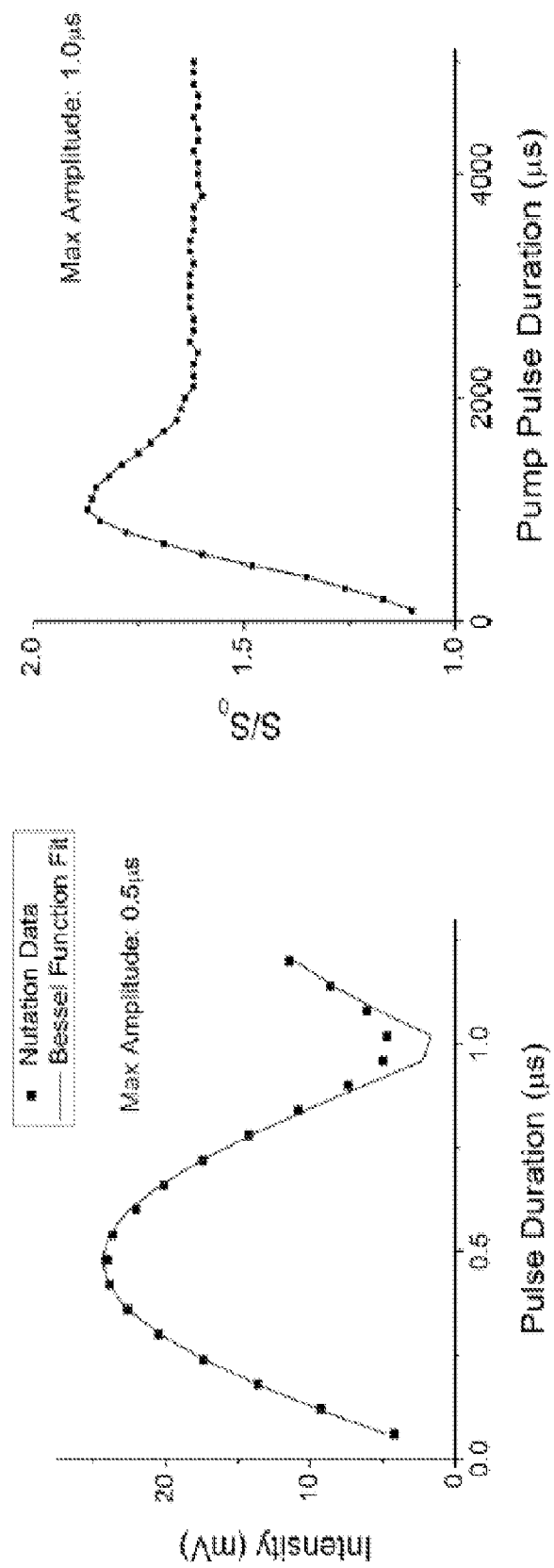
FIGS. 6A and 6B illustrate generally illustrative examples of received signal strength as a function of excitation or pump pulse duration for a single-color technique and a two-color technique, respectively.

One- and Two-Color Variable Pulse Duration Population Transfer Measurements to Estimate the Dipole Moment An intensity of a spectral transition is determined by the "strength" of the transition, determined by its dipole moment and the rotational quantum numbers, the sample temperature, and the amount of substance present. Accordingly, an independent measurement can be used to extract the dipole moment contribution. Such extraction can be performed such as by measuring the transition signal as a function of the excitation pulse duration. The maximum signal occurs for an approximate "π/2" pulse condition, as in nuclear magnetic resonance (NMR) spectroscopy, and is proportional to the dipole moment. An illustrative example of such a technique is shown in FIGS. 6A and 6B. As described above, a pulse pattern waveform can be used to measure the pulse duration signal dependence in a single measurement signal collection event. This measurement can also be performed in a two-color implementation where the effect of the variable excitation pulse duration is detected through the changes in the signal of a transition in double-resonance, as shown in FIGS. 5A and 5B.

FIGS. 6A and 6B illustrate generally illustrative examples of received signal strength as a function of excitation or pump pulse duration for a single-color technique and a two-color technique, respectively. For the single-color technique of FIG. 6A, a damped sinusoidal oscillation models a Bessel function, and the first maximum represents the "π/2" pulse duration ($t_{\pi/2}$), 500 ns for the measurement of OCS that is shown, and is related to the excitation Rabi frequency, $\omega_{Rabi}$ [$(\pi/2)/t_{\pi/2}$], which is directly proportional to the transition dipole moment. An alternative way to measure the Rabi frequency is shown in FIG. 6B and uses the two-color technique described in FIG. 4A where the first signal maximum occurs for a "π" pulse duration and $\omega_{Rabi}$ [$(\pi)/t_\pi$]. This pulse duration is 1000 ns in FIG. 6B, or twice the pulse duration of FIG. 6A, as expected. The method of FIG. 6B may give more accurate results in the case of dense spectra where there may be spectral overlap because it filters the spectral response for a single molecule using the principles of two-color double-resonance spectroscopy.

Mass Estimation by Determination of the Doppler Contribution

Determination of molecular mass facilitates chemical identification. In mm-wave rotational spectroscopy analysis of gases at thermal equilibrium, it is possible to determine the mass from the Doppler contribution to the line shape. In the frequency domain, this analysis can be complicated because the Doppler and collisional contributions to the line shape occur as a convolution. There are many approximations to the frequency domain line shape for the problem of line shape analysis. In one approach, the goal is to measure the collisional contribution for a molecule of known molecular weight. However, such existing techniques of collisional contribution analysis are not applicable in cases where neither the Doppler nor the collisional contributions are known.

In the time domain, the FID occurs as the product of a Doppler dephasing and, to a good approximation, an exponential contribution from the collisional relaxation. This approximation produces a Voigt line shape profile in the frequency domain and can neglect effects such as speed-dependent relaxation rates. For rotational spectroscopy, the approximation that the collisional time scales $T_1$ (population) and $T_2$ are equal is expected to hold. A functional form for the FID can be represented by Equation (1) below:

$$E(t) \propto \cos(\omega t) e^{\frac{-t}{T_1}} e^{-(\frac{t}{2s})^2} \quad (1)$$

with $$s = \frac{c}{\omega}\sqrt{\frac{m}{2kT}} \quad (2)$$

where ω can represent the transition frequency, $T_1$ can represent the collisional relaxation time constant, and s can represent the Doppler dephasing time constant that depends on the molecular mass, m. The time-domain Fourier transform spectrometer of the examples described herein can provide at least two ways to independently measure the collisional contribution to the FID decay making the extraction of the molecular mass through the Doppler contribution more reliable.

Single Color Pulse Echoes

Using time-domain pulse echo methods, a collisional contribution to the FID decay can be directly measured. A pulse echo excitation sequence, including a set of two pulses with variable time separation, is shown illustratively in FIG. 7 (such as can be provided using the apparatus of FIG. 1 or 2). The analysis of these results and their use in estimating the mass from the FID is shown illustratively in FIGS. 8A and 8B. The results shown correspond to a J=22–21 transition of OCS. Emission decays by dephasing (by Doppler) and relaxation (predominantly by collision). A first excitation pulse induces a signal 702 which Doppler dephases rapidly (the FID), seen as fast decay to a flat line in the time-domain plot. The second excitation pulse induces a new signal 704 while simultaneously rephasing the previous signal. The rephasing appears as an echo 706 with a time delay from the second pulse equal to the time between the two excitation pulses. As the pulse time separation increases, the appearance of the echo is correspondingly delayed, as shown in the progression of examples (A), (B), and (C) in FIG. 7. The echo disappears when the measuring time exceeds the collisional relaxation time.

Figure 7:
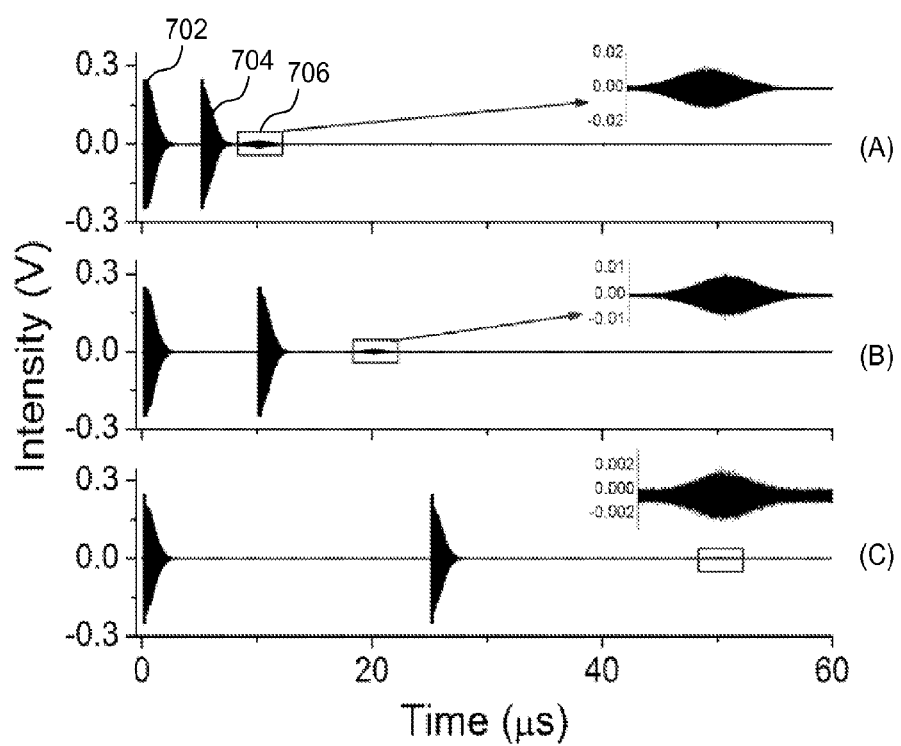
FIG. 7 depicts a plot illustrating a pulse echo technique, such as can be performed using the apparatus of FIG. 1 or 2, such as to determine a collisional relaxation time.
Figure 8B:
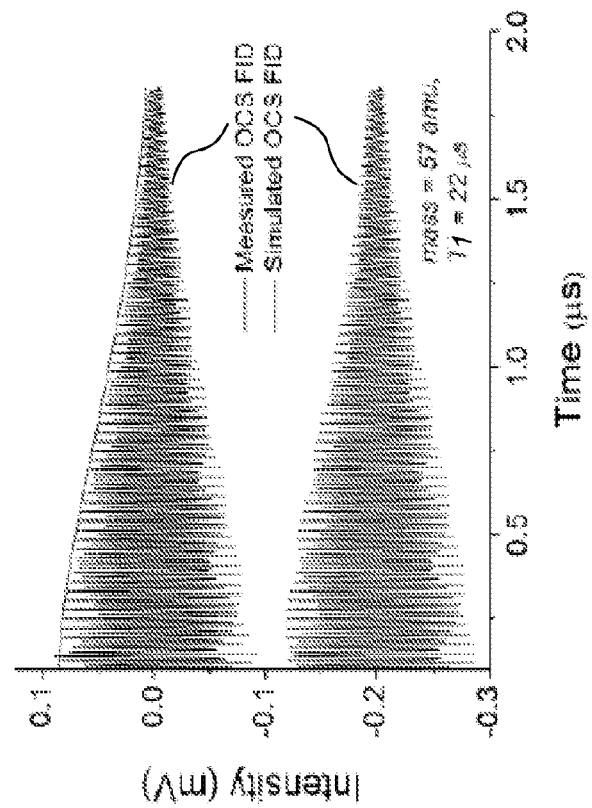
FIG. 8B illustrates generally an illustrative example comparing a measured FID and a simulated FID determined using a molecular mass and a collision relaxation time constant $T_1$.
Figure 8A:
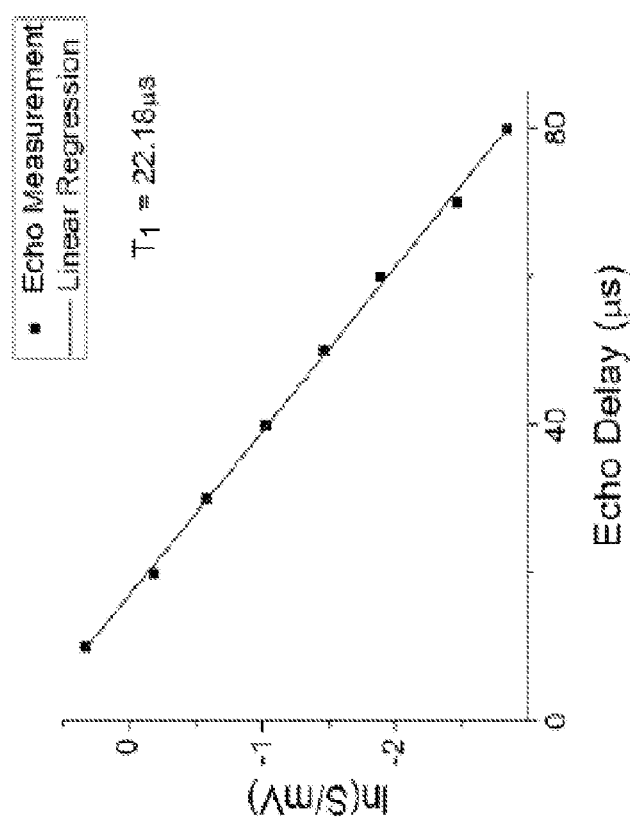
FIG. 8A illustrates generally an illustrative example of an echo signal strength versus echo delay, such as can be obtained using the pulse echo technique described in relation to FIG. 7.

FIG. 8A illustrates generally an illustrative example of an echo signal strength versus echo delay, such as can be obtained using the pulse echo technique described in relation to FIG. 7. FIG. 8B illustrates generally an illustrative example comparing a measured FID and a simulated FID determined using a molecular mass and a collision relaxation time constant $T_1$. In particular, FIG. 8A depicts a logarithmic plot of the echo signal strength with increasing time delay. Collisions induce an exponential relaxation. Linear regression analysis of the measurements yields a collision relaxation time constant ($T_1$) of 22.2 microseconds compared to a literature value of 25.4 microseconds. FIG. 8B depicts a plot illustrating the measured FID and a simulated FID calculated based on molecular mass and $T_1$. The best fit determines a mass of 57 atomic mass units (amu), a result within 5% of the known mass of OCS (60 amu). Accordingly, the molecular mass can be determined even for an unknown sample, such as using information obtained about the collisional relaxation time.

One- and Two-Color Population Recovery Measurements

The pulse echo method has the advantage that it measures exactly the collisional $T_1$ contribution to the FID signal being analyzed. Once the collisional contribution to the decay of the FID is known, the Doppler contribution can be accurately determined. However, the echo signals can be weak and this may limit the applicability of the method. In rotational spectroscopy, it has been shown that $T_1$ (population relaxation) and $T_2$ (dephasing) time scales are essentially identical, so the estimation of the collision contribution to the FID decay can also be made using population recovery techniques. In this technique, a first "pump" pulse creates a transient population difference.

The recovery of this population difference to equilibrium can be measured by applying a probe pulse at variable time separations from the pump pulse. The probe pulse can be resonant with either the same transition used in the pump step (one-color) or a transition in double-resonance (two-color). The results for both one-color and two-color saturation recovery measurements in OCS are shown, respectively, below in FIGS. 9A and 9B.

Figure 9B:
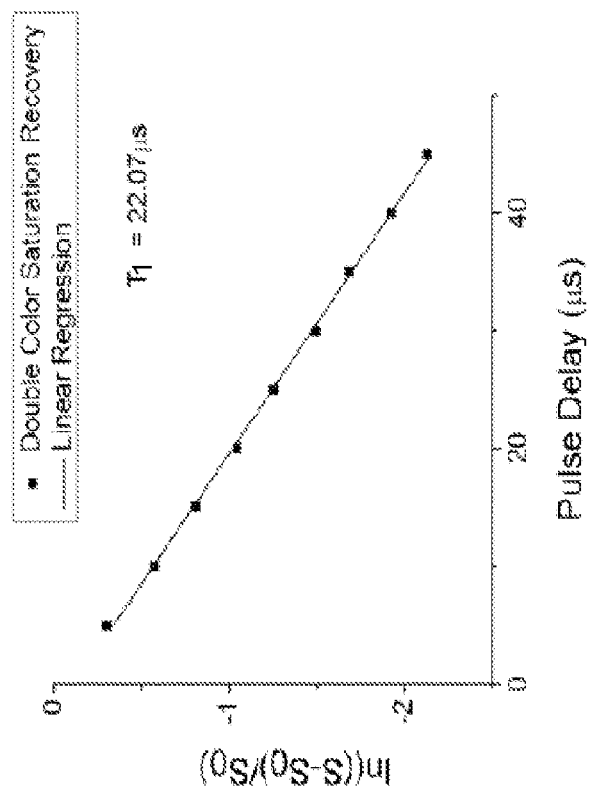
FIGS. 9A and 9B illustrate generally illustrative examples of collision relaxation times determination via experiment, such as can be obtained using a single-color and a dual-color saturation-excitation time delay technique, respectively.
Figure 9A:
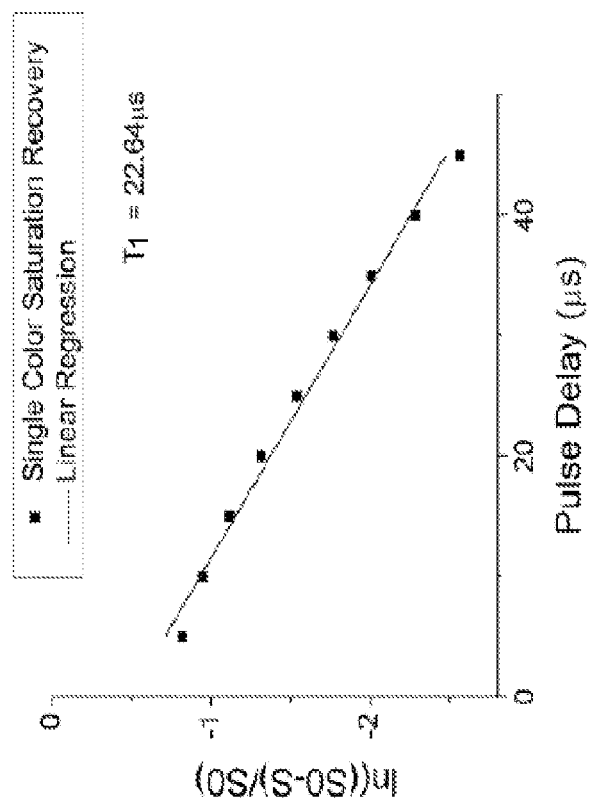

FIGS. 9A and 9B illustrate generally illustrative examples of collision relaxation times determination via experiment, such as can be obtained using a single-color and a dual-color saturation-excitation time delay technique, respectively. The pump pulse induces a population equalization, which decays exponentially with time. The effect is measured by monitoring the log of the modulated signal (y-axis), rather than an echo signal, as the probe pulse is delayed in time. The amplitude of the modulated signal can be determined by digitizing the time-domain modulated signal, performing a Fourier transform on the time-domain representation, then determining a magnitude of the transformed representation at the transition frequency of interest. Alternatively, an amplitude of the modulated signal can be determined in the time domain by performing an amplitude determination or fit to a digitized time-series representative of the modulated FID. The collision relaxation time constant ($T_1$), is determined to be 22.64 microseconds for the single color experiment and 22.07 microseconds for the two-color experiment, compared to a literature value of 25.4 microseconds.

The two-color implementation depicted in FIG. 9B shows better exponential decay behavior (linear in this log plot) as compared to FIG. 9A, and the time scale is the same as observed for the pulse echo measurement above. The relaxation times from the pulse echo (FIG. 7) and two-color population recovery experiments (FIG. 9B) are in agreement with each other and the literature value of OCS self-relaxation.

Generally, the technique of FIG. 9A can be used if at least a single molecular transition frequency is known (e.g., "probe" and "pump" pulses can include the same excitation frequency applied to the sample). Such a transition can be known if the species being characterized is known, or such a transition can be empirically determined using techniques described herein by obtain a spectrum via Fourier transforming a digitized representation of the FID elicited from the sample via pulsed excitation. The technique of FIG. 9A can be referred to as a "single-color" measurement.

By contrast, the technique of FIG. 9B can be used if different frequencies are used for the "pump" and "probe" excitations. This technique can be referred to as a "two-color" measurement. Such frequencies (corresponding to transitions that share a common energy level) can be known if the species being characterized is known, or can be identified using the double-resonance examples described elsewhere herein. Without being bound by theory, use of such double resonances is believed to enhance measurement accuracy of the mass estimation approach as compared to the single-color approach, because of the better exponential decay behavior mentioned above.

Figure 10:
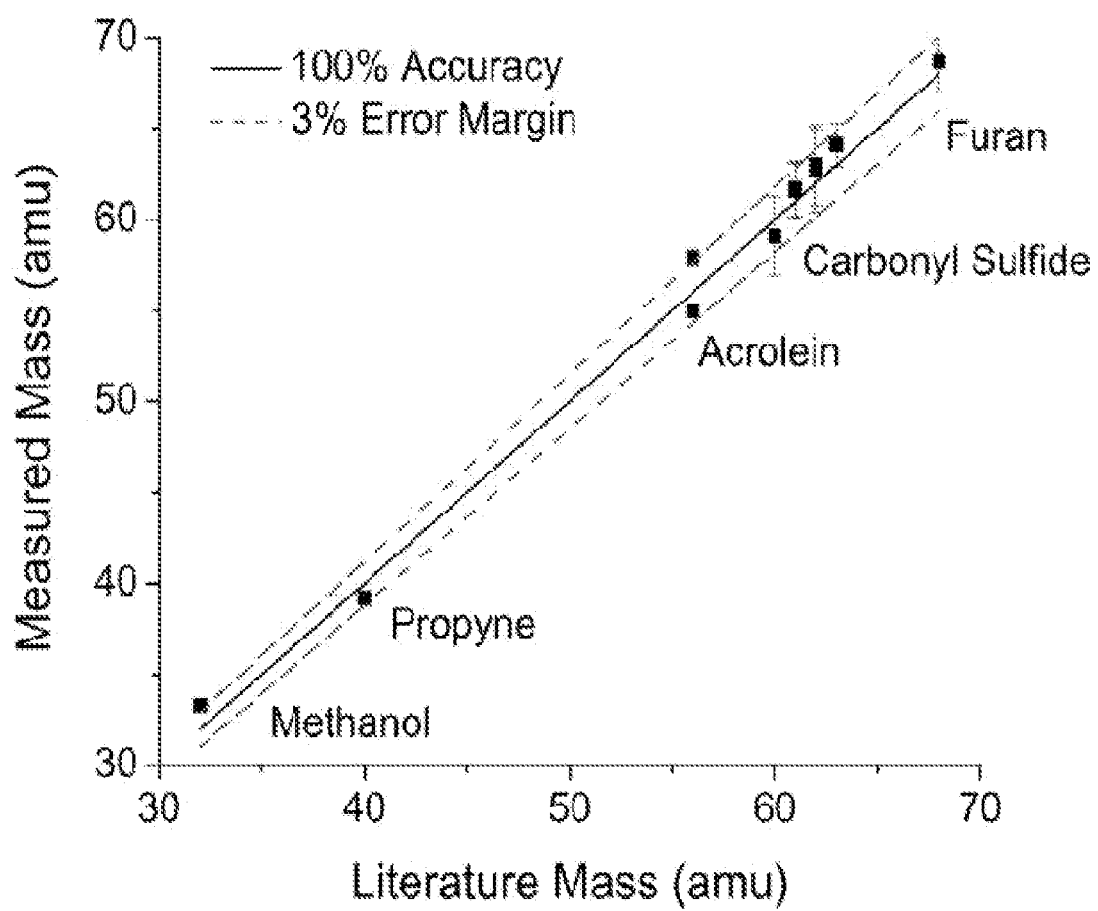
FIG. 10 illustrates generally an illustrative example of various mass estimates of different molecules, where such mass estimates have been experimentally obtained using molecular rotational spectroscopy without requiring a priori knowledge of the molecular species.

FIG. 10 illustrates generally an illustrative example of various mass estimates of different molecules, where such mass estimates have been experimentally obtained using molecular rotational spectroscopy without requiring a priori knowledge of the molecular species. These measurements used the pulse echo method to independently measure the collisional relaxation time ($T_1$) as described above in relation to FIGS. 8A and 8B. The accuracy of the method is shown to be ±3% for the set of molecules shown in Table 1, which also includes the individual measurement results.

TABLE 1

Molecular Mass Estimation by FID Decay Modeling

| Molecule | Literature Mass (amu) | Measured Mass (amu) | Fractional Absolute Error |
|---|---|---|---|
| Methanol | 32.03 | 33.3 | 0.04 |
| Propyne | 40.03 | 39.2 | 0.02 |
| Acrolein | 56.03 | 57.9 | 0.03 |
| Acrolein | 56.03 | 55 | 0.02 |

TABLE 1-continued

Molecular Mass Estimation by FID Decay Modeling

| Molecule | Literature Mass (amu) | Measured Mass (amu) | Fractional Absolute Error |
|---|---|---|---|
| Carbonyl Sulfide-main | 59.97 | 59.1 | 0.01 |
| Carbonyl Sulfide-$^{13}$C | 60.97 | 61.7 | 0.01 |
| Carbonyl Sulfide-$^{33}$S | 60.97 | 61.6 | 0.01 |
| Carbonyl Sulfide-$^{34}$S | 61.96 | 62.7 | 0.01 |
| Carbonyl Sulfide-$^{18}$O | 61.97 | 63.0 | 0.02 |
| Carbonyl Sulfide-$^{13}$C$^{34}$S | 62.96 | 64.1 | 0.02 |
| Furan | 68.03 | 68.7 | 0.01 |

As described above, the measurement technique uses a pulse echo sequence to independently measure the collisional lifetime ($T_1$). This $T_1$ value can then be used to fit the time-domain free induction decay (FID) signal to determine the Doppler contribution to the dephasing (e.g., using the representation of Equations 1 and 2). For example, using the Doppler contribution and the known sample temperature, the molecular mass can be extracted such as via identification of an mass value through regression analysis that provides the best fit to the measured FID, after determination and using the measured $T_1$ in the regression analysis. This technique can be applied to any transition observed in the gas sample and does not require any foreknowledge about the molecular carrier of the transition or the quantum mechanical energy levels involved in the transition (sometimes called the "assignment"). In FIG. 10, the dashed lines show a ±3% error on the mass determination. The error bars on the mass determination are model fitting errors from the numerical fit technique. For carbonyl sulfide, near mass 60 amu, four different isotopologues were measured in natural abundance. The analysis results are also listed in Table 1 and illustrate that the techniques described herein are also useful for identification and discrimination of isotopologues.

Various Notes

Example 1 can include or use subject matter (such as an apparatus, a method, a means for performing acts, or a device readable medium including instructions that, when performed by the device, can cause the device to perform acts), such as can include exciting a gaseous sample using a first pulsed excitation and a second pulsed excitation each including energy in a mm-wave range of frequencies, the first pulsed excitation and the second pulsed excitation spaced apart in time by a specified duration that is varied between respective measurement cycles, and the first and second pulsed excitations generated at least in part using a frequency multiplier to provide the mm-wave range of frequencies.

Example 1 can include obtaining respective time-domain representations elicited from the gaseous sample in response to the first and second pulsed excitations corresponding to the respective measurement cycles, determining a collisional relaxation time constant using the respective time-domain representations of the response, and estimating a molecular mass of a species included in the gaseous sample at least in part using the determined collisional relaxation time constant.

Example 2 can include, or can optionally be combined with the subject matter of Example 1, to optionally include estimating the molecular mass of the species included in the gaseous sample without requiring foreknowledge of the molecular carrier.

Example 3 can include, or can optionally be combined with the subject matter of one or any combination of Examples 1 or 2 to optionally include frequencies of the first and second excitations that are different.

Example 4 can include, or can optionally be combined with the subject matter of one or any combination of Examples 1 through 3 to optionally include a frequency multiplier comprising an active multiplier chain.

Example 5 can include, or can optionally be combined with the subject matter of one or any combination of Examples 1 through 4 to optionally include estimating the molecular mass including obtaining a time-domain representation of a free induction decay of the gaseous sample in response to excitation using the first and second pulsed excitations and determining a molecular mass using an analytical model to provide a best fit to an envelope of the free induction decay.

Example 6 can include, or can optionally be combined with the subject matter of one or any combination of Examples 1 through 5 to optionally include first and second excitations generated at least in part using a solid-state synthesizer circuit.

Example 7 can include, or can optionally be combined with the subject matter of one or any combination of Examples 1 through 6 to optionally include a solid-state synthesizer circuit having a first output to provide a first frequency to be upconverted at least in part using the frequency multiplier to provide the first pulsed excitation and a second output to provide a second frequency to be upconverted at least in part using the frequency multiplier to provide the second pulsed excitation.

Example 8 can include, or can optionally be combined with the subject matter of one or any combination of Examples 6 or 7 to optionally include a solid-state synthesizer circuit configured to provide continuous wave (CW) output, where the first and second pulsed excitations are provided at least in part by pulse modulating the CW output of the solid-state synthesizer circuit according to a specified modulation pattern defining durations of the first and second pulsed excitations.

Example 9 can include, or can optionally be combined with the subject matter of one or any combination of Examples 1 through 8 to optionally include frequencies of the first and second excitations specified to provide an integer number of cycles during a measurement period.

Example 10 can include, or can optionally be combined with the subject matter of one or any combination of Examples 1 through 9 to optionally include a frequency of one or more of the first pulsed excitation or the second pulsed excitation selected at least in part using information obtained from a spectrum obtained via Fourier transformation of a series of obtained time-domain representations of respective responses elicited from the gaseous sample in response to a sequence of pulsed excitations having frequencies offset from one another.

Example 11 can include, or can optionally be combined with the subject matter of one or any combination of Examples 1 through 10 to optionally include a spectrum is obtained at least in part by concatenating a series of Fourier transforms each corresponding to an obtained time-domain response elicited from the gaseous sample in response to a respective pulsed excitation frequency.

Example 12 can include, or can optionally be combined with the subject matter of one or any combination of Examples 1 through 11 to optionally include probing the gaseous sample using a probe frequency selected to modulate an intensity of the observed peak according in response to a presence of a prior excitation of the sample, the prior excitation using a pump frequency that is different from the probe frequency.

Example 13 can include, or can optionally be combined with the subject matter of Example 12, to optionally include determining a presence or absence of a species within the gaseous species at least in part using information about whether modulation of the intensity of the observed peak occurs in the presence of the prior excitation.

Example 14 can include, or can optionally be combined with the subject matter of one or any combination of Examples 1 through 13 to include, subject matter (such as an apparatus, a method, a means for performing acts, or a machine readable medium including instructions that, when performed by the machine, that can cause the machine to perform acts), such as can include exciting a gaseous sample using pulsed excitations each including energy in a mm-wave range of frequencies, using timing that is varied between respective measurement cycles, the pulsed excitations generated at least in part using a frequency multiplier to provide the mm-wave range of frequencies, obtaining respective time-domain representations elicited from the gaseous sample in response to the pulsed excitation, determining a collisional relaxation time constant using the respective time-domain representations of the response, and estimating a molecular mass of a species included in the gaseous sample at least in part using the determined collisional relaxation time constant.

Example 15 can include, or can optionally be combined with the subject matter of Example 14, to optionally include obtaining a time-domain representation of a free induction decay of the gaseous sample, and determining a molecular mass using an analytical model to provide a best fit to an envelope of the free induction decay.

Example 16 can include, or can optionally be combined with the subject matter of one or any combination of Examples 14 or 15 to optionally include frequencies of the pulsed excitations specified to provide an integer number of cycles during a measurement period.

Example 17 can include, or can optionally be combined with the subject matter of one or any combination of Examples 1 through 16 to include, subject matter (such as an apparatus, a method, a means for performing acts, or a machine readable medium including instructions that, when performed by the machine, that can cause the machine to perform acts), such as can include a spectrometer comprising an multiplier chain (AMC) light source including a radio-frequency (RF) input and a mm-wave output, a frequency source including an output in communication with the RF input of the AMC light source, and a pulse modulator configured to pulse-modulate the output of the frequency source, where an output frequency of the frequency source is specified to provide an integral number of oscillation cycles during a measurement cycle, the measurement cycle established at least in part using the pulse modulator.

Example 18 can include, or can optionally be combined with the subject matter of Example 17, to optionally include a frequency source having at least two outputs having respective output frequencies.

Example 19 can include, or can optionally be combined with the subject matter of one or any combination of Examples 17 or 18 to optionally include a dual-conversion superheterodyne circuit configured to down-convert a response elicited from a gaseous sample, where a mm-wave output of the AMC light source is configured to provide a signal for excitation of the gaseous sample.

Example 20 can include, or can optionally be combined with the subject matter of one or any combination of Examples 17 through 19 to optionally include a processor circuit coupled to the pulse modulator and configured control the pulse modulator to provide a first "pump" excitation pulse having a first specified duration, a second "probe" excitation pulse having a second specified duration, and having a specified separation in time from the first "pump" excitation pulse.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method, comprising:
    exciting a gaseous sample using a first pulsed excitation and a second pulsed excitation each including energy in a mm-wave range of frequencies, the first pulsed excitation and the second pulsed excitation spaced apart in time by a specified duration that is varied between respective measurement cycles, and the first and second pulsed excitations generated at least in part using a frequency multiplier to provide the mm-wave range of frequencies;
    obtaining respective time-domain representations elicited from the gaseous sample in response to the first and second pulsed excitations corresponding to the respective measurement cycles;
    determining a collisional relaxation time constant using the respective time-domain representations of the response; and
    estimating a molecular mass of a species included in the gaseous sample at least in part using the determined collisional relaxation time constant.

2. The method of claim 1, wherein the estimating the molecular mass of the species included in the gaseous sample does not require foreknowledge of the molecular carrier.

3. The method of claim 1, wherein frequencies of the first and second excitations are different.

4. The method of claim 1, wherein the frequency multiplier comprises an active multiplier chain.

5. The method of claim 1, wherein estimating the molecular mass includes obtaining a time-domain representation of a free induction decay of the gaseous sample in response to excitation using the first and second pulsed excitations; and
    determining a molecular mass using an analytical model to provide a best fit to an envelope of the free induction decay.

6. The method of claim 1, wherein the first and second excitations are generated at least in part using a solid-state synthesizer circuit.

7. The method of claim 6, wherein the solid-state synthesizer circuit includes a first output to provide a first frequency to be upconverted at least in part using the frequency multiplier to provide the first pulsed excitation; and
    a second output to provide a second frequency to be upconverted at least in part using the frequency multiplier to provide the second pulsed excitation.

8. The method of claim 6, wherein the wherein the solid-state synthesizer circuit is configured to provide continuous wave (CW) output; and
wherein the first and second pulsed excitations are provided at least in part by pulse modulating the CW output of the solid-state synthesizer circuit according to a specified modulation pattern defining durations of the first and second pulsed excitations.

9. The method of claim 1, wherein frequencies of the first and second excitations are specified to provide an integer number of cycles during a measurement period.

10. The method of claim 1, wherein a frequency of one or more of the first pulsed excitation or the second pulsed excitation is selected at least in part using information obtained from a spectrum obtained via Fourier transformation of a series of obtained time-domain representations of respective responses elicited from the gaseous sample in response to a sequence of pulsed excitations having frequencies offset from one another.

11. The method of claim 10, wherein the spectrum is obtained at least in part by concatenating a series of Fourier transforms each corresponding to an obtained time-domain response elicited from the gaseous sample in response to a respective pulsed excitation frequency.

12. The method of claim 10, comprising probing the gaseous sample using a probe frequency selected to modulate an intensity of the observed peak according in response to a presence of a prior excitation of the sample, the prior excitation using a pump frequency that is different from the probe frequency.

13. The method of claim 12, wherein presence or absence of a species within the gaseous species is determined at least in part using information about whether modulation of the intensity of the observed peak occurs in the presence of the prior excitation.

14. A non-transitory processor-readable medium including instructions that, when performed by a processor circuit, cause an apparatus to:
excite a gaseous sample using pulsed excitations each including energy in a mm-wave range of frequencies, using timing that is varied between respective measurement cycles, the pulsed excitations generated at least in part using a frequency multiplier to provide the mm-wave range of frequencies;
obtain respective time-domain representations elicited from the gaseous sample in response to the pulsed excitation;
determine a collisional relaxation time constant using the respective time-domain representations of the response; and
estimate a molecular mass of a species included in the gaseous sample at least in part using the determined collisional relaxation time constant.

15. The non-transitory processor-readable medium of claim 14, wherein the instructions to estimate the molecular mass include instructions to:
obtain a time-domain representation of a free induction decay of the gaseous sample; and
determine a molecular mass using an analytical model to provide a best fit to an envelope of the free induction decay.

16. The non-transitory processor-readable medium of claim 14, wherein frequencies of the pulsed excitations are specified to provide an integer number of cycles during a measurement period.

17. An spectrometer comprising:
a multiplier chain light source including a radio-frequency (RF) input and a mm-wave output;
a frequency source including an output in communication with the RF input of the multiplier chain light source;
a pulse modulator configured to pulse-modulate the output of the frequency source;
a receiver configured to provide a digital representation of a response elicited from a gaseous sample in response to excitation of the gaseous sample, the mm-wave output configured to provide a signal for the excitation; and
a processor circuit configured to:
determine a collisional relaxation time constant using a time-domain representation of the response elicited from the sample; and
estimate a molecular mass of a species included in the gaseous sample at least in part using the determined collisional relaxation time constant;
wherein an output frequency of the frequency source is specified to provide an integral number of oscillation cycles during a measurement cycle, the measurement cycle established at least in part using the pulse modulator.

18. The spectrometer of claim 17, wherein the frequency source includes at least two outputs having respective output frequencies.

19. The spectrometer of claim 17, wherein the receiver comprises a dual-conversion superheterodyne circuit configured to down-convert the response elicited from a gaseous sample.

20. The spectrometer of claim 17, wherein the processor circuit is coupled to the pulse modulator and is configured control the pulse modulator to provide:
a first "pump" excitation pulse having a first specified duration; and
a second "probe" excitation pulse having a second specified duration, and having a specified separation in time from the first "pump" excitation pulse.

* * * * *